US012758483B2

(12) United States Patent
Wong et al.

(10) Patent No.: US 12,758,483 B2
(45) Date of Patent: Oct. 13, 2026

(54) ANTIBACTERIAL AND MINERALIZING COMPOSITIONS AND METHODS OF USE THEREOF

(71) Applicant: The University of Hong Kong, Hong Kong (CN)

(72) Inventors: Hai Ming Wong, Hong Kong (CN); Quan Li Li, Hong Kong (CN); Li Zhou, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 536 days.

(21) Appl. No.: 18/546,733

(22) PCT Filed: Jan. 20, 2022

(86) PCT No.: PCT/CN2022/072965
§ 371 (c)(1),
(2) Date: Aug. 16, 2023

(87) PCT Pub. No.: WO2022/174715
PCT Pub. Date: Aug. 25, 2022

(65) Prior Publication Data
US 2025/0275905 A1 Sep. 4, 2025

Related U.S. Application Data

(60) Provisional application No. 63/149,961, filed on Feb. 16, 2021.

(51) Int. Cl.
*A61K 8/64* (2006.01)
*A61Q 11/00* (2006.01)
*C07K 14/47* (2006.01)

(52) U.S. Cl.
CPC ................ *A61K 8/64* (2013.01); *A61Q 11/00* (2013.01); *C07K 14/47* (2013.01)

(58) Field of Classification Search
CPC ........ A61Q 11/00; C07K 14/47; C07K 19/00; A61K 38/17
USPC .................................................... 424/49, 401
IPC ....................................................... A61Q 11/00
See application file for complete search history.

(56) References Cited

U.S. PATENT DOCUMENTS

| | | | |
|---|---|---|---|
| 2,913,373 | A | 11/1959 | Weisz et al. |
| 3,975,514 | A | 8/1976 | Weisz |
| 4,083,955 | A | 4/1978 | Grabenstetter et al. |
| 4,548,809 | A | 10/1985 | Fung et al. |
| 5,631,228 | A | 5/1997 | Oppenheim et al. |
| 5,948,390 | A | 9/1999 | Nelson et al. |
| 6,117,417 | A | 9/2000 | Wicks et al. |
| 6,264,925 | B1 | 7/2001 | Fuglsang et al. |
| 6,706,256 | B2 | 3/2004 | Lawlor |
| 6,740,311 | B2 | 5/2004 | White et al. |
| 9,937,365 | B2 | 4/2018 | Chopra et al. |
| 10,314,771 | B2 | 6/2019 | Dehghan et al. |
| 10,406,078 | B2 | 9/2019 | Jiao et al. |
| 2001/0002252 | A1 | 5/2001 | Gallopo et al. |
| 2002/0064505 | A1 | 5/2002 | Rosenberg |
| 2003/0007937 | A1 | 1/2003 | Lawlor |
| 2003/0124068 | A1 | 7/2003 | Atsushi et al. |
| 2003/0175216 | A1 | 9/2003 | Rosenberg |
| 2007/0154410 | A1 | 7/2007 | Kim |
| 2015/0065435 | A1 | 3/2015 | Sarikaya et al. |
| 2017/0022256 | A1 | 1/2017 | Cheng et al. |
| 2017/0211131 | A1 | 7/2017 | Cheng et al. |
| 2025/0296961 | A1 | 9/2025 | Wong et al. |

FOREIGN PATENT DOCUMENTS

| | | | | |
|---|---|---|---|---|
| CN | 1222345 | A | 7/1999 | |
| CN | 1385145 | A | 12/2002 | |
| JP | H01275521 | A | 11/1989 | |
| JP | H02157215 | A | 6/1990 | |
| JP | H08113519 | A | 5/1996 | |
| JP | 2004051511 | A | 2/2004 | |
| WO | 9409752 | A1 | 5/1994 | |
| WO | 2006135601 | A1 | 12/2006 | |
| WO | WO-2016044940 | A1 * | 3/2016 | ............... C07K 7/06 |

OTHER PUBLICATIONS

International Search Report received for PCT Patent Application No. PCT/CN2022/072965, mailed on Apr. 19, 2022, 7 pages.
Aas , et al., "Bacteria of Dental Caries in Primary and Permanent Teeth in Children and Young Adults", J Clin Microbiol., vol. 46, No. 4, Apr. 2008, pp. 1407-1417.
Carillo , et al., "The Multiple Sequence Alignment Problem in Biology", SIAM J Applied Math., vol. 48, No. 5, Oct. 1988, pp. 1073-1082.
Genpept , "UniProtKB/Swiss-Prot: P15516.2", Accession No. P15516, Mar. 27, 2024, 12 pages.
Mehdawi , et al., "High strength re-mineralizing, antibacterial dental composites with reactive calcium phosphates", Dent Mater., vol. 29, No. 4, Apr. 2013, pp. 473-484.
Merrifield, R. B., "Solid Phase Peptide Synthesis. I. The Synthesis of a Tetrapeptide", J. Am. Chem. Soc., vol. 85, No. 14, 1963, pp. 2149-2154.

(Continued)

*Primary Examiner* — Walter E Webb
(74) *Attorney, Agent, or Firm* — Pabst Patent Group LLP

(57) ABSTRACT

Peptides that bind with high affinity to oral cavity surfaces, such as tooth enamel, have been discovered. The peptides exhibit antibacterial and mineralizing abilities, and are useful in many aspects of oral care. A preferred peptide includes the amino acid sequence AKRHHGYKRKFH-SpSp. The peptides can be included in oral care compositions such as toothpastes and mouthwashes. The oral care compositions can be used in methods to treat or prevent diseases or conditions induced by acidophilic oral bacteria. Exemplary methods include reducing or preventing tooth decay or demineralization, biofilm or dental plaque formation, and/or bacterial adhesion to a tooth surface; and promoting mineralization of teeth surfaces.

16 Claims, 12 Drawing Sheets

Specification includes a Sequence Listing.

(56) References Cited

OTHER PUBLICATIONS

Needleman , et al., “A General Method Applicable to the Search for Similarities in the Amino Acid Sequence of Two Proteins”, J. Mol. Biol., vol. 48, No. 3, Mar. 1970, pp. 443-453.
Pepperney , et al., “Antibacterial Peptides: Opportunities for the Prevention and Treatment of Dental Caries”, Probiotics Antimicrob Proteins., vol. 3, No. 2, Jun. 2011, pp. 68-96.
Puri , et al., “How Does It Kill?: Understanding the Candidacidal Mechanism of Salivary Histatin 5”, Eukaryot Cell., vol. 13, No. 8, Aug. 2014, pp. 958-964.
Russell, et al., “Innate Humoral Defense Factors”, Mucosal Immunology, 2005, pp. 73-93.
Wang , et al., “Preventive effects of the novel antimicrobial peptide Nal-P-113 in a rat Periodontitis model by limiting the growth of Porphyromonas gingivalis and modulating IL-1β and TNF-α production”, BMC Complement Altern Med., vol. 17, No. 1: 426, Aug. 29, 2017, 10 pages.
Zhou , et al., “Anti-Biofouling Coatings on the Tooth Surface and Hydroxyapatite”, Int J Nanomedicine., vol. 15, Nov. 13, 2020, pp. 8963-8982.
Zhou , et al., “Constructing an Antibiofouling and Mineralizing Bioactive Tooth Surface to Protect against Decay and Promote Self-Healing”, ACS Appl Mater Interfaces., vol. 12, No. 2, Jan. 15, 2020, pp. 3021-3031.

* cited by examiner

Peak Table

Detector A 214nm

| Peak# | Ret. Time | Area | Height | Area% |
|---|---|---|---|---|
| 1 | 10.976 | 2266178 | 431040 | 98.001 |
| 2 | 11.198 | 46225 | 6306 | 1.999 |
| Total | | 2312403 | 437346 | 100.000 |

Processed Channel: 2487Channel 1

| | Processed Channel | Retention Time (min) | Area | % Area | Height |
|---|---|---|---|---|---|
| 1 | 2487Channel 1 | 8.144 | 29003 | 0.69 | 2772 |
| 2 | 2487Channel 1 | 8.534 | 145923 | 3.39 | 11922 |
| 3 | 2487Channel 1 | 8.805 | 4185155 | 95.62 | 458723 |
| 4 | 2487Channel 1 | 9.200 | 15832 | 0.38 | 2886 |

SEQUENCE LISTING

```
<160> NUMBER OF SEQ ID NOS: 7

<210> SEQ ID NO 1
<211> LENGTH: 24
<212> TYPE: PRT
<213> ORGANISM: Homo sapiens

<400> SEQUENCE: 1

Asp Ser His Ala Lys Arg His His Gly Tyr Lys Arg Lys Phe His Glu
1               5                   10                  15

Lys His His Ser His Arg Gly Tyr
            20


<210> SEQ ID NO 2
<211> LENGTH: 12
<212> TYPE: PRT
<213> ORGANISM: Artificial Sequence
<220> FEATURE:
<223> OTHER INFORMATION: P-113 peptide

<400> SEQUENCE: 2

Ala Lys Arg His His Gly Tyr Lys Arg Lys Phe His
1               5                   10


<210> SEQ ID NO 3
<211> LENGTH: 51
<212> TYPE: PRT
<213> ORGANISM: Homo sapiens

<400> SEQUENCE: 3

Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
        35                  40                  45

Tyr Asp Asn
    50


<210> SEQ ID NO 4
<211> LENGTH: 14
<212> TYPE: PRT
<213> ORGANISM: Artificial Sequence
<220> FEATURE:
<223> OTHER INFORMATION: P-113-DPS peptide
<220> FEATURE:
<221> NAME/KEY: MOD_RES
<222> LOCATION: (13)..(13)
<223> OTHER INFORMATION: The Serine is a phosphorylated serine
<220> FEATURE:
<221> NAME/KEY: MOD_RES
<222> LOCATION: (14)..(14)
<223> OTHER INFORMATION: The Serine is a phosphorylated serine

<400> SEQUENCE: 4
```

-continued

```
Ala Lys Arg His His Gly Tyr Lys Arg Lys Phe His Ser Ser
1               5                   10


<210> SEQ ID NO 5
<211> LENGTH: 27
<212> TYPE: PRT
<213> ORGANISM: Artificial Sequence
<220> FEATURE:
<223> OTHER INFORMATION: P-113-SK peptide

<400> SEQUENCE: 5

Ala Lys Arg His His Gly Tyr Lys Arg Lys Phe His Ser Lys His Lys
1               5                   10                  15

Gly Gly Lys His Lys Gly Gly Lys His Lys Gly
            20                  25


<210> SEQ ID NO 6
<211> LENGTH: 13
<212> TYPE: PRT
<213> ORGANISM: Artificial Sequence
<220> FEATURE:
<223> OTHER INFORMATION: P-113-DA peptide
<220> FEATURE:
<221> NAME/KEY: MOD_RES
<222> LOCATION: (13)..(13)
<223> OTHER INFORMATION: 3,4-dihydroxyphenethylamine linked to aspartic
      acid

<400> SEQUENCE: 6

Ala Lys Arg His His Gly Tyr Lys Arg Lys Phe His Asp
1               5                   10


<210> SEQ ID NO 7
<211> LENGTH: 25
<212> TYPE: PRT
<213> ORGANISM: Artificial Sequence
<220> FEATURE:
<223> OTHER INFORMATION: Sp-H5 Peptide
<220> FEATURE:
<221> NAME/KEY: MOD_RES
<222> LOCATION: (1)..(1)
<223> OTHER INFORMATION: The Serine is a phosphoserine

<400> SEQUENCE: 7

Ser Asp Ser His Ala Lys Arg His His Gly Tyr Lys Arg Lys Phe His
1               5                   10                  15

Glu Lys His His Ser His Arg Gly Tyr
            20                  25
```

ANTIBACTERIAL AND MINERALIZING COMPOSITIONS AND METHODS OF USE THEREOF

This application is a National Phase application under 35 U.S.C. 371 of PCT/CN2022/072965, filed Jan. 20, 2022, and claims priority to and the benefit of U.S. Provisional Patent Application No. 63/149,961 filed on Feb. 16, 2021, the entire content of which are incorporated herein by reference for all purpose in their entirety.

REFERENCE TO SEQUENCE LISTING

The Sequence Listing submitted as a.txt file named "UHK_01004_ST25.txt" created on Jan. 9, 2024, and having a size of 2,894 bytes is hereby incorporated by reference pursuant to 37 C.F.R. §§ 1.77 (b) (5) (i) and 1.825 (c).

FIELD OF THE INVENTION

The disclosed invention is generally in the field of oral care, and specifically, relates to methods and compositions for preventing and treating dental caries.

BACKGROUND OF THE INVENTION

Tooth decay is a significant oral health problem that affects millions of individuals around the world. Tooth decay can cause significant tooth damage compromising the esthetics and function of teeth, requiring extensive dental treatment. Due to a fear of the dental drill and anesthetic injections, most people do not attend dental appointments regularly. As such, a majority of caries lesions are not restored at the initial stage and gradually become larger and symptomatic. Traditional caries treatment is an invasive therapy, including preparing a cavity on sound dental tissue and restoring it with conventional materials, such as amalgam and composite resin. However, due to the differences in properties between dental tissue and artificial materials, the long-term performance of the restored tooth is suboptimal. Thus, prevention and reversal of dental caries prior to cavity formation presents a difficult challenge for dentistry.

Dental caries results from an ecological imbalance within the caries pathogen biofilm that favors specific acidogenic pathogens, such as *Streptococcus mutans* (*S. mutans*), which decompose sugars to produce acids which interrupt the tooth surface mineralization balance and induce demineralization of dental hard tissues. For example, when bacteria metabolize fermentable carbohydrates, acids are produced as a byproduct that lower the pH value of oral and plaque fluids, therefore creating an acidic oral environment. The bacterial acids (including particularly lactic acid) may then, among other things, leach minerals out of tooth structures within the oral cavity. Dental caries is typically characterized by this demineralization of mineral components and the decomposition of the organic matrix from one or more calcified structures of a tooth: enamel, dentin, or cementum. Therefore, caries is theoretically preventable and repairable, for example by inhibiting caries pathogen biofilm formation, reducing dental hard tissue demineralization, and inducing its remineralization.

There are numerous strategies for caries management. The use of chemical surface modifications as nonspecific coatings, such as polyethylene glycol and zwitterion, has demonstrated anti-adhesive properties in vitro. However, their low surface densities and sensitivity to oxidative damage might result in failure of antibacterial adhesion for long-term applications. Commercial products, e.g., toothpaste and mouthwashes, containing chemicals such as antibiotics, chlorhexidine, and fluorides are commonly used to prevent caries pathogen biofilm formation. However, antibiotics are unsuitable for daily use because of the potential to result in antibiotic resistance and subsequent side effects, while the efficacy of chlorhexidine is low. Fluorides show certain antibacterial activities only at very high concentrations. It is difficult to continuously sustain their topical concentrations on the tooth, and their toxicity is also a concern. Some fluoride- and calcium phosphate-based reagents such as casein phosphopeptide-amorphous calcium phosphate have been used to induce mineral deposits on tooth surfaces, but the deposits do not actually become part of the enamel microstructure. Furthermore, most of the existing anti-caries agents are mono-functional. Thus, there is an urgent and ongoing need for agents and methods to improve prevention and treatment of dental caries.

BRIEF SUMMARY OF THE INVENTION

It is an object of the invention to provide compositions and methods for the prevention and treatment of dental caries (tooth decay).

It is an object of the invention to provide antibacterial and/or mineralizing compositions useful for dental care.

It is an object of the invention to provide compositions and methods to prevent adhesion of microorganisms to a tooth surface.

It is another object of the invention to provide compositions and methods for protecting teeth against an acidic environment.

It is a further object of the invention to provide compositions and methods to prevent or reduce tooth demineralization and/or induce tooth remineralization.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Peptides that bind with high affinity to oral cavity surfaces, such as tooth enamel, have been discovered. The peptides exhibit both anti-biofouling and mineralizing abilities, and as such, are useful in many aspects of oral care.

In particular, disclosed is an isolated peptide containing an antimicrobial domain and a phosphoserine domain. The antimicrobial domain can include a histatin 5 segment. A histatin 5 segment can be or include a histatin 5 protein, a variant thereof, a portion thereof, or a variant of a portion thereof. Typically, the antimicrobial domain is histatin 5 (e.g., human histatin 5) or a portion thereof. For example, in some forms, the histatin 5 or portion thereof includes the amino acid sequence DSHAKRHHGYKRKFHEKHHSHRGY (SEQ ID NO:1) or a sequence having at least 90% sequence identity to DSHAKRHHGYKRKFHEKHHSHRGY (SEQ ID NO:1).

Preferably, the antimicrobial domain is or contains a portion of human histatin 5, such as AKRHHGYKRKFH (SEQ ID NO:2) or a sequence having at least 90% sequence identity to AKRHHGYKRKFH (SEQ ID NO:2).

The phosphoserine domain is or includes a phosphorylated serine. In some forms, the phosphoserine domain includes two or more phosphorylated serines (Sp). Typically, the phosphoserine domain is positioned at the C-terminus of the isolated peptide. A preferred peptide of the disclosure includes the amino acid sequence AKRHHGYKRKFH-SpSp (SEQ ID NO:4), wherein each Sp independently represents a phosphorylated serine.

Preferably, the peptide is capable of binding to a tooth surface, such as enamel. In some forms, upon contact with an oral cavity (e.g., tooth surface) the isolated peptide binds to tooth enamel, reduces or prevents tooth decay or demineralization, reduces or prevents bacterial biofilm formation on a tooth surface, reduces or prevents dental plaque formation, reduces or prevents bacterial adhesion to a tooth surface, promotes (e.g., induces or increases) mineralization of a tooth surface, inhibits growth and/or proliferation of bacteria in the oral cavity, or combinations thereof. For example, in some forms, upon coating or otherwise being applied to a tooth surface the peptide attracts calcium and/or phosphate ions (e.g., from saliva) to promote generation of new crystal deposits on the tooth surface.

Also disclosed are compositions including one or more of the disclosed peptides. For example, pharmaceutical compositions including an effective amount of the peptide or a plurality of copies of the peptide and a pharmaceutically acceptable excipient are provided. Typically, the excipient is acceptable for administration to oral cavity. Oral care compositions or devices including the isolated peptide or a plurality of copies of the isolated peptide are provided. Exemplary compositions or devices include, without limitation, mouthwashes, toothpastes, dental creams, oral sprays, rinses, gargles, gums, tablets, oral lozenges, dental floss, tooth whitening strips or solutions, cleaning solutions, toothpicks, toothbrushes, varnishes, and restorative materials such as composite resin.

Methods of using the peptides and compositions thereof are also provided. An exemplary method involves applying a disclosed oral care composition or device containing the peptide to the teeth and/or oral cavity of a subject. In some forms, applying the peptide to the teeth and/or oral cavity of a subject can be used to reduce or prevent tooth decay, repair tooth decay, reduce or prevent enamel demineralization, promote enamel mineralization, or combinations thereof.

For example, disclosed is a method of reducing or preventing and/or repairing tooth decay in a subject in need thereof by contacting the subject's teeth and/or oral cavity with a peptide having the sequence AKRHHGYKRKFH-SpSp (SEQ ID NO:4) or a sequence having at least 90% sequence identity to AKRHHGYKRKFH-SpSp (SEQ ID NO: 4). Also provided is method of reducing or preventing enamel demineralization and/or promoting enamel mineralization in a subject in need thereof by contacting the subject's teeth and/or oral cavity with a peptide having the sequence AKRHHGYKRKFH-SpSp (SEQ ID NO:4) or a sequence having at least 90% sequence identity to AKRHHGYKRKFH-SpSp (SEQ ID NO:4).

In some forms of the foregoing methods, the peptide or a plurality of copies of the peptide are included in a composition or device selected from mouthwash, toothpaste, dental cream, oral spray, a rinse, a gargle, a gum, a tablet, an oral lozenge, dental floss, a tooth whitening strip or solution, a cleaning solution, a toothpick, a toothbrush, a varnish, or composite resin. In some forms, the peptide is in an amount effective to reduce or prevent tooth decay, reduce or prevent bacterial biofilm formation, reduce or prevent dental plaque formation, reduce or prevent bacterial adhesion to tooth surfaces, inhibit growth and/or proliferation of oral bacteria, induce or increase enamel mineralization, or combinations thereof. In some forms, the bacteria contained in the biofilm, the bacteria whose adhesion is reduced or prevented, and/or whose growth and/or proliferation is inhibited is selected from *Streptococcus mutans, Streptococcus faecalis, Streptococcus sobrinus, Lactobaccilus acidophilus, Lactobacillus casei*, or combinations thereof.

Additional advantages of the disclosed methods will be set forth in part in the description which follows, and in part will be understood from the description, or can be learned by practice of the disclosed methods and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods and compositions and together with the description, serve to explain the principles of the disclosed method and compositions.

FIG. 8A is a graph showing proliferation of MC3T3-E1 treated with peptides at different concentrations for 24 h. *p<0.001, compared with control. FIG. 8B is a graph showing proliferation of MC3T3-E1 on 8 μM mL-1 peptide-coated enamel surfaces for 1 and 3 days.

DETAILED DESCRIPTION OF THE INVENTION

Figure 1A:
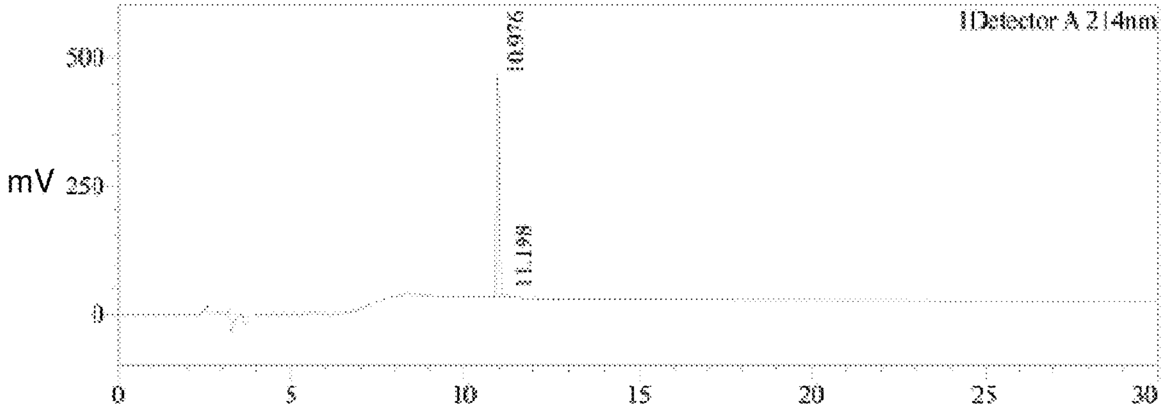
FIGS. 1A-1D are a series of HPLC chromatograms of P113 (FIG. 1A), P113-DPS (FIG. 1B), P113-DA (FIG. 1C), and P113-SK (FIG. 1D) at 220 nm.
Figure 1B:
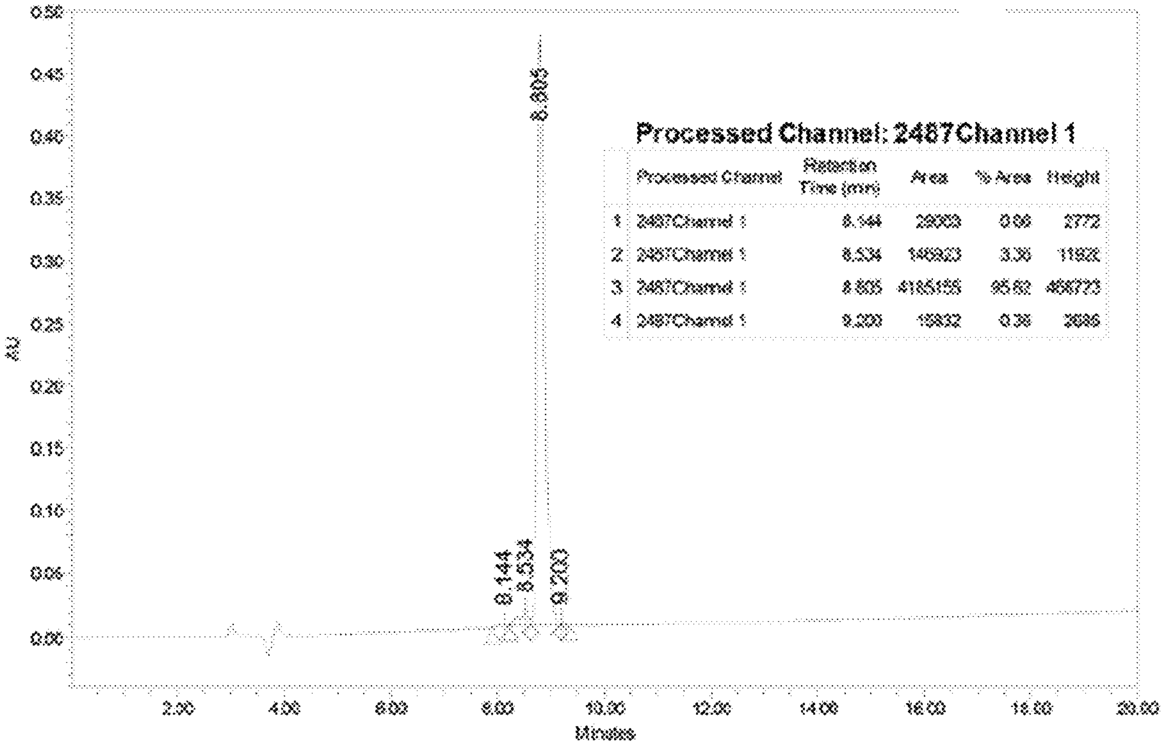
Figure 1C:
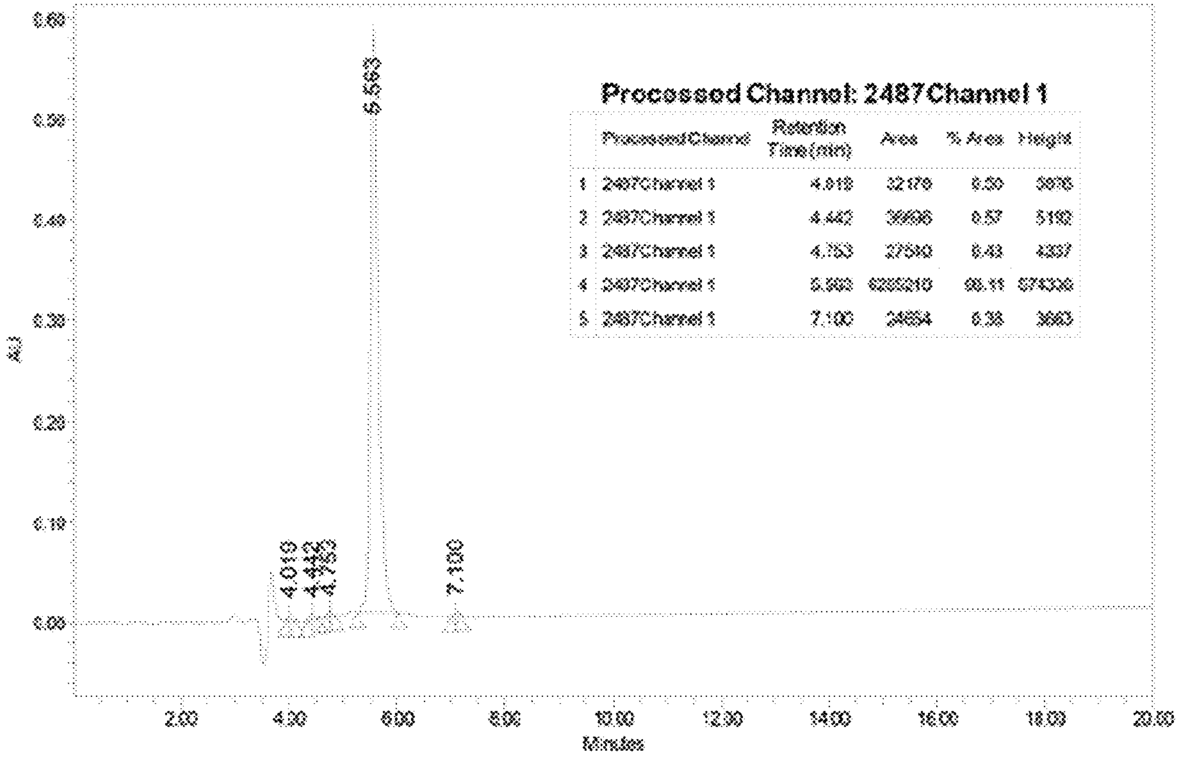
Figure 1D:
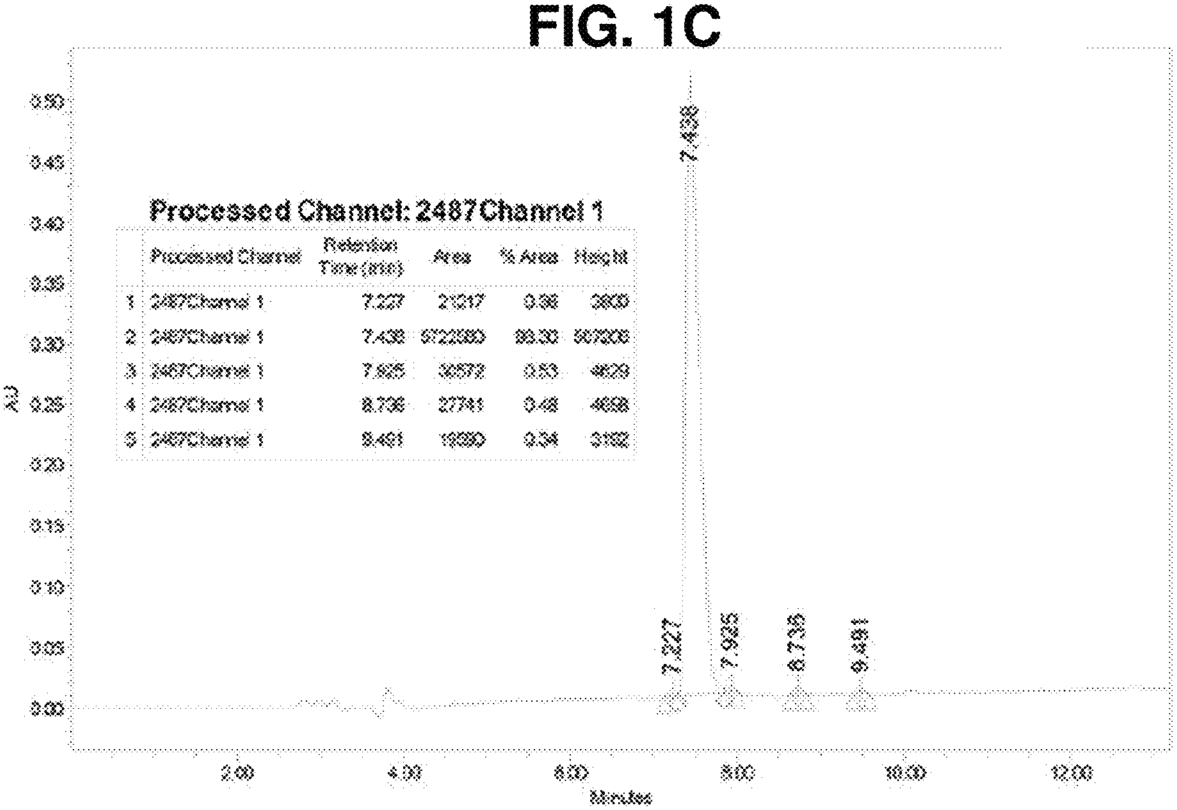
Figure 2A:
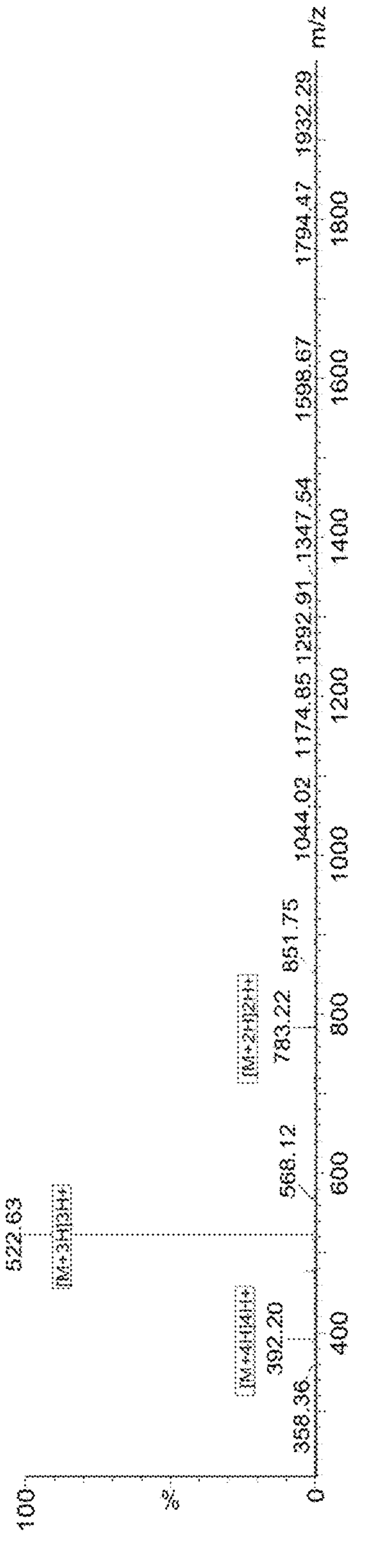
FIGS. 2A-2D are a series of MS spectra of P113 (FIG. 2A), P113-DPS (FIG. 2B), P113-DA (FIG. 2C), and P113-SK (FIG. 2D).
Figure 2B:
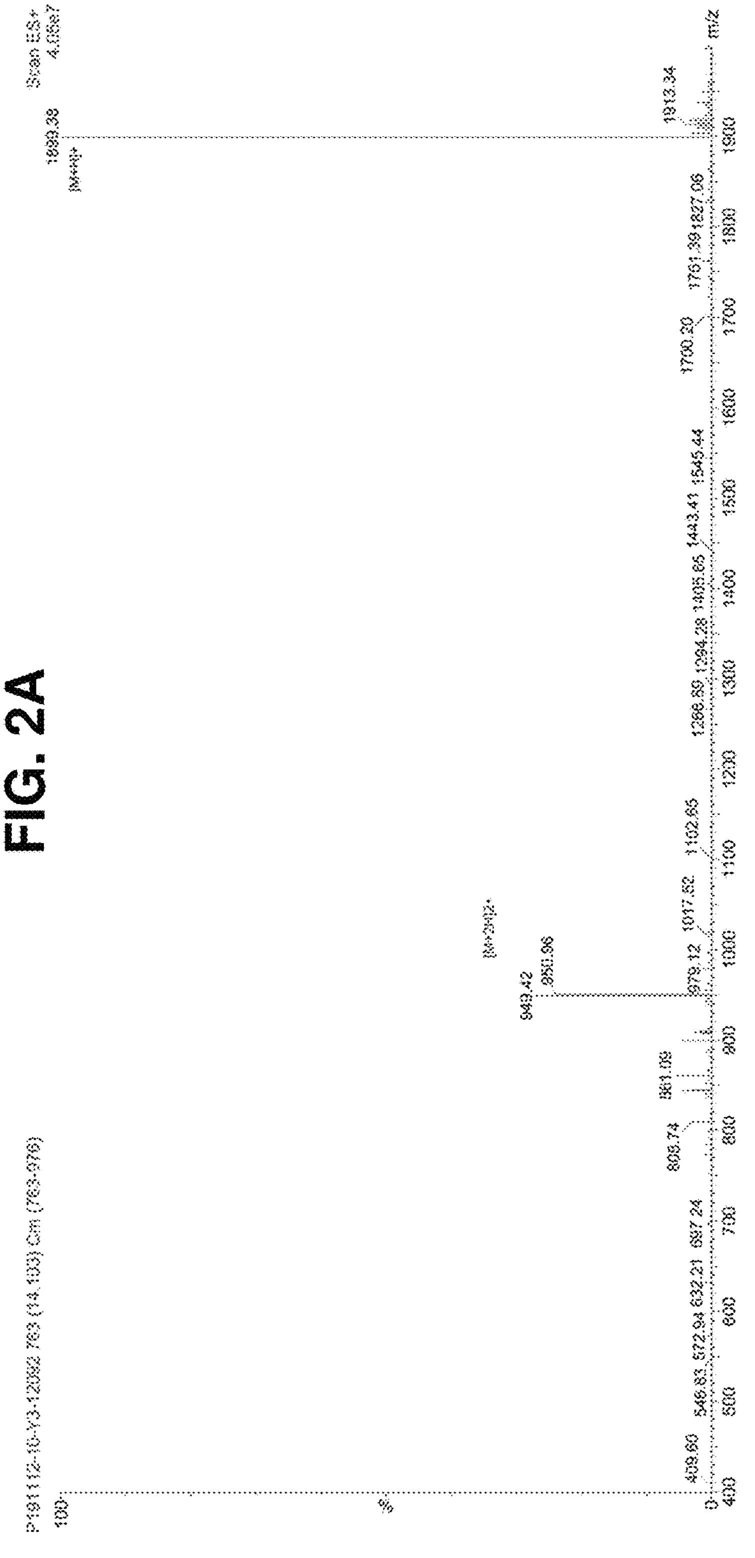
Figure 2C:
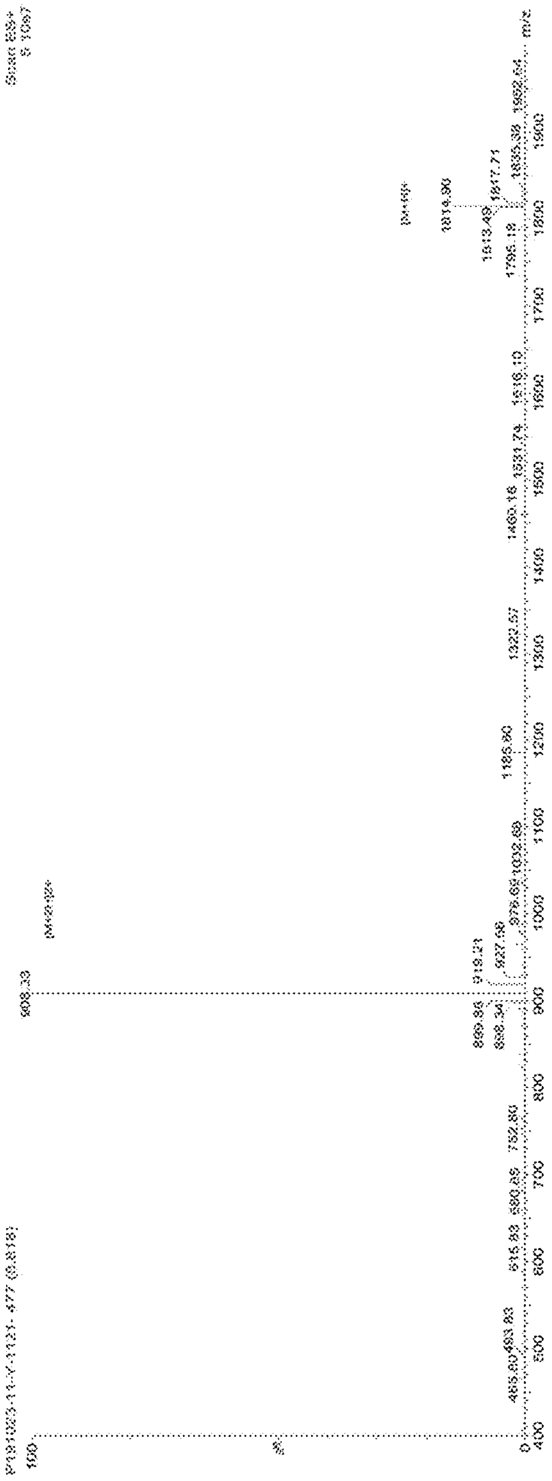
Figure 2D:

The disclosed methods and compositions can be understood more readily by reference to the following detailed description of particular embodiments and the Examples included therein and to the Figures and their previous and following description.

Microorganisms reside in the oral cavity and easily accumulate on tooth surfaces. Some bacterial microorganisms produce a local acidic environment, which ultimately causes demineralization of tooth hard tissues, such as enamel, thereby causing dental caries. Despite the prevalence of oral care products, there is a continuing need for agents that can prevent microorganism adhesion to tooth surfaces, protect teeth against bacteria-induced acidic environment, and reverse demineralization of teeth.

To this end, peptides that bind with high affinity to oral cavity surfaces, such as tooth enamel, have been developed. The working Examples describe development and functional characterization of a number of peptides, including their ability to adsorb to enamel, to prevent bacterial biofilm formation, to kill planktonic bacteria, to reduce demineralization, and to promote remineralization. In particular, the peptide P-113-DPS which contains P-113, a fragment of the antimicrobial histatin 5 peptide, and a diphosphserine domain (which can chelate free $Ca^{2+}$ to promote tooth in situ mineralization) grafted to the C-terminus of P-113 outperformed all other peptides tested. The antibacterial activity of P-113-DPS was stronger than other peptides such as P-113-DA, P-113-SK, and P-113. Among the peptides tested, P-113-DPS showed the highest binding affinity to the tooth surface, the strongest suppression of acid-induced corrosion, and the thickest newly regenerated crystals. P-113-DPS adsorbs onto enamel surfaces within 20 minutes, and subsequent adhesion of microorganisms to the enamel surface is reduced. Thus, P-113-DPS and functionally equivalent peptides can be used to promote overall oral health, including preventing or treating dental caries.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

I. Definitions

As used herein in reference to the peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation. A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography.

As used herein, the term "mineralization" refers to the introduction of or restoration of minerals to dental hard tissues within the oral cavity. The term not only includes remineralizing areas that are hypomineralized, but may also include mineralizing and strengthening tissues that may be healthy, existing, and/or newly erupted.

The term "tooth surface" refers to a surface comprised of tooth enamel (typically exposed after professional cleaning or polishing) or tooth pellicle (an acquired surface comprising salivary glycoproteins). As used herein, the terms "enamel" and "tooth enamel" will refer to the highly mineralized tissue which forms the outer layer of the tooth. The enamel layer is composed primarily of crystalline calcium phosphate (hydroxyapatite) along with water and some organic material. As used herein, the terms "pellicle" and "tooth pellicle" will refer to the thin film (typically ranging from about 1 μm to about 200 μm thick) derived from salivary glycoproteins which forms over the surface of the tooth crown.

By "pharmaceutically acceptable" is meant a material that can be administered to a subject without causing undesirable biological effects or interacting in a deleterious manner with any of the other components of the pharmaceutical composition in which it is contained.

As used herein, the term "carrier" or "excipient" refers to an organic or inorganic ingredient, natural or synthetic inactive ingredient in a formulation, with which one or more active ingredients are combined.

The term "binding" refers to the interaction between a corresponding pair of molecules or portions thereof that exhibit mutual affinity or binding capacity, typically due to specific or non-specific binding or interaction, including, but not limited to, biochemical, physiological, and/or chemical interactions. By "specific binding" or "selective binding" is meant that the molecules, such as peptides, that are able to bind to or recognize a binding partner (or a limited number of binding partners) to a substantially higher degree than to other, similar biological entities. For example, the molecule binds preferentially to the target as compared to non-target. Selective binding to is generally characterized by at least a two-fold greater binding to a target, as compared to a non-target. A molecule can be characterized by, for example, 5-fold, 10-fold, 20-fold or more preferential binding to the target as compared to one or more non-targets.

By "contact" or "contacting" is meant to allow or promote a state of immediate proximity or physical association between at least two elements. For example, to contact a tooth surface with a peptide is to provide physical association between the tooth surface and the peptide.

The term, "in vitro" refers to an artificial environment and to processes or reactions that occur within an artificial environment. In vitro environments include, but are not limited to, in solution or suspension, and cell cultures. The term "in vivo" refers to in or associated with an organism, such as an animal.

The term "effective amount," as used herein, refers to an amount of an agent that is sufficient to elicit a desired biological and/or a pharmacologic response. In some forms, an "effective amount" or "therapeutically effective amount" means a quantity sufficient to alleviate or ameliorate one or more symptoms of a disorder, disease, or condition being treated. As will be appreciated by the skilled artisan, the effective amount of an agent, e.g., an isolated peptide, may vary depending on various factors, for example, the desired biological response, the site being targeted, and on the agent being used.

As used herein, the term "subject" means any individual, organism or entity. The subject can be a vertebrate, for example, a mammal (e.g., rat, rabbit, mouse, dog, cat, goat, pig, or horse). Thus, the subject can be a human. The term does not denote a particular age or sex. Thus, adult and newborn subjects, whether male or female, are intended to be covered. The subject may be healthy or suffering from or susceptible to a disease, disorder or condition. A patient refers to a subject afflicted with a disease or disorder. The term "patient" includes human and veterinary subjects.

As used herein, "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevention" or "preventing" means to administer a composition to a subject or a system at risk for or having a predisposition for one or more symptoms caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, the terms "reduce" and "inhibit" mean to decrease an activity, response, condition, disease, or other biological parameter. This can include, but is not limited to, the complete ablation of the activity, response, condition, or disease. It is understood that this is typically in relation to a standard or expected value. The reduction or inhibition may be a 10, 20, 30, 40, 50, 60, 70, 80, 90, 100%, or any amount of reduction in between as compared to native or control levels. In some forms, inhibition or reduction is relative to a state prior to administration of one or more therapeutics. In some forms, inhibition or reduction is relative to a control that is not administered one or more therapeutics.

The term "peptide" refers to a class of compounds composed of amino acids chemically bound together. In general, the amino acids are chemically bound together via amide linkages (CONH); however, the amino acids can be bound together by other chemical bonds known in the art. For example, the amino acids can be bound by amine linkages. Peptide as used herein includes oligomers of amino acids and small and large peptides, including polypeptides. Thus, the terms "protein," "peptide," and "polypeptide" are used interchangeably herein. The protein, peptide, or polypeptide can be of any size, structure, or function. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "percent (%) sequence identity" describes the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

"Identity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988). Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). In some forms, the default parameters can be used to determine the identity for the polynucleotides or polypeptides of the present disclosure.

In some forms, the % sequence identity of a given nucleic acid or amino acid sequence C to, with, or against a given nucleic acid or amino acid sequence D (which can alternatively be phrased as a given sequence C that has or includes a certain % sequence identity to, with, or against a given sequence D) is calculated as follows: 100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approximately +/−10%; in other forms the values may range in value either above or below the stated value in a range of approximately +/−5%; in other forms the values may range in value either above or below the stated value in a range of approximately +/−2%; in other forms the values may range in value either above or below the stated value in a range of approximately +/−1%. The preceding ranges are intended to be made clear by context, and no further limitation is implied.

II. Compositions

Disclosed are compositions containing one or more peptides that bind to oral cavity surfaces, such as tooth enamel. The peptides have anti-biofouling and mineralizing abilities, and as such, are useful in many aspects of oral care. For example, the peptides can prevent microorganism adhesion to oral cavity surfaces, protect teeth against an acid environment, and/or reduce, prevent or reverse enamel demineralization.

A. Peptides

Disclosed are isolated peptides capable of binding to oral cavity surfaces either in vitro or in vivo. Preferably, the peptide is capable of binding to a tooth surface, such as enamel. In some forms, upon contact with an oral cavity (e.g., tooth surface) the isolated peptide binds to tooth enamel, reduces or prevents tooth decay or demineralization, reduces or prevents bacterial biofilm formation on a tooth surface, reduces or prevents dental plaque formation, reduces or prevents bacterial adhesion to a tooth surface, promotes (e.g., induces or increases) mineralization of a tooth surface, inhibits growth and/or proliferation of bacteria in the oral cavity, or combinations thereof. The ability to promote mineralization is based on the peptide's affinity for minerals such as calcium and phosphate ions in the oral cavity. For example, in some forms, upon coating or otherwise being applied to a tooth surface (e.g., enamel), the peptide attracts calcium and/or phosphate ions in the oral cavity (e.g., from saliva) to promote generation of new crystal deposits on the tooth surface.

In some forms, the peptide contains two or more domains. The domains can confer one or more distinct functions to the peptide. For example, in some forms, the peptide contains an antimicrobial domain and a dentotropic (tooth-binding) moiety or domain. In preferred forms, the peptide contains an antimicrobial domain and a phosphoserine moiety or domain (e.g., a diphosphoserine domain (DPS)).

In some forms, the antimicrobial domain is or is derived from a naturally occurring protein. Preferably, the antimicrobial domain is or is derived from a histatin protein or a portion thereof. Histatins are a family of at least 12 small, histidine-rich, cationic peptides secreted into human saliva by salivary glands with significant in vitro antimicrobial activity, especially against fungi such as *Candida*. Histatins 1, 3, and 5 are the most abundant, and they have been credited with most of the anticandidal activity, histatin 5 being the most effective. Histatins 1 and 3 are encoded by HIS1 and HIS2 genes, respectively; histatin 5 is a proteolytic product of histatin 3, and all the other histatins are believed to arise from histatins 1 and 3 by proteolytic processing. Besides killing the wild-type *C. albicans*, histatins have been found to be effective in the in vitro killing of *Candida* species resistant to the commonly used antimycotics, fluconazole, and amphotericin B, as well as of *C. neoformans*. See Russell M W, et al., Chapter 5-Innate Humoral Defense Factors, Mucosal Immunology (Third Edition), Academic Press, 2005, pages 73-93.

Among all histatins, histatin 5 has the most potent fungicidal activity against pathogenic fungi, including *Candida albicans* and other medically important *Candida* species, such as *Candida kefyr, Candida krusei*, and *Candida parapsilosis*, as well as *Cryptococcus neoformans* and *Aspergillus fumigatus* (Puri S. and Edgerton M., Eukaryot Cell, 13(8):958-64 (2014)). Histatin 5 potentially inhibits almost 100% of the *C. albicans* cells from germinating into more-virulent hyphae. Inhibitory and bactericidal activities of histatins have also been shown against various bacteria, including *S. mutans, P. gingivalis, A. actinomycetemcomitans, P. aeruginosa, E. coli*, and *St. aureus* (Russel M W., et al.). Histatins as natural antimicrobial peptides show little or no toxicity toward mammalian cells and a low tendency to elicit resistance and thus have great potential to be developed into a novel class of antimicrobials, although few in vivo studies have been published.

The amino acid sequence of various histatins are known in the art. For example, the amino acid sequence of histatin 3 (from which histatin 5 is proteolytically processed), available from the Uniprot database under ID No. P15516, is MKFFVFALILALMLSMTGAD-SHAKRHHGYKRKFHEKHHSHRGYRSNYLYDN (SEQ ID NO:3). In preferred forms, the antimicrobial domain is or is derived from histatin 5 (e.g., human histatin 5). An exemplary amino acid sequence of human histatin 5 is DSHAKRHHGYKRKFHEKHHSHRGY (SEQ ID NO:1). Thus, in some forms, the antimicrobial domain has the amino acid sequence DSHAKRHHGYKRKFHEK-HHSHRGY (SEQ ID NO:1).

In some forms, the antimicrobial domain is or contains a portion of histatin 5. For example, in some preferred forms, the antimicrobial domain has the amino acid sequence AKRHHGYKRKFH (SEQ ID NO:2).

In some forms, the antimicrobial domain includes an amino acid sequence having at least 80%, 85%, 90%, 91%, 92%, 93%, 94%, 95%, 96%, 97%, 98%, 99% or more sequence identity to the sequence provided in any of SEQ ID NOs: 1-3. For example, in some preferred forms, the antimicrobial domain has an amino acid sequence having at least 90% sequence identity to DSHAKRHHGYKRKFHEKHHSHRGY (SEQ ID NO:1). In some preferred forms, the antimicrobial domain has an amino acid sequence having at least 90% sequence identity to AKRHHGYKRKFH (SEQ ID NO:2).

In preferred forms, the disclosed isolated peptide contains a phosphoserine moiety or domain. Typically, the phosphoserine domain includes one or more phosphorylated serines (Sp). For example, the phosphoserine domain can include 1, 2, 3, 4, 5 or more phosphorylated serines. In preferred forms, the phosphoserine domain includes two phosphorylated serines (referred to herein as a diphosphoserine domain (DPS)).

The antimicrobial domain and phosphoserine domain can be arranged in any orientation within the peptide. For example, the phosphoserine domain can be at the N- or C-terminus of the peptide. In some forms, the peptide conforms to the following architecture/structure:

$NH_2$[antimicrobial domain]-[phosphoserine domain] COOH; or $NH_2$[phosphoserine domain]-[antimicrobial domain] COOH wherein $NH_2$ is the N-terminus of the peptide, and COOH is the C-terminus of the peptide. In some forms, the "-" used in the general architecture above indicates the presence of an optional linker. In some forms, the "-" used in the general architecture above does not indicate the presence of a linker, but is rather used to visually designate the start of one domain from the end of another. Preferably, the phosphoserine domain is positioned at the C-terminus of the peptide.

In preferred forms, the peptide includes the amino acid sequence AKRHHGYKRKFH-SpSp (SEQ ID NO:4), wherein each Sp independently represents a phosphorylated serine.

In some forms, the isolated peptides disclosed herein do not include a linker. For example, in some forms, the P-113-DPS peptide AKRHHGYKRKFH-SpSp (SEQ ID NO: 4) does not include a linker between the antimicrobial domain and phosphoserine domain. In some forms, the P-113-SK peptide AKRHHGYKRKFH-SKHKGGKHKGGKHKG (SEQ ID NO:5) does not include a linker between the antimicrobial domain and surface binding (SK) domain.

In some forms, a linker is present between one or more domains within the isolated peptide (e.g., between an antimicrobial domain and a dentotropic domain (e.g., phosphoserine domain)). For example, in some forms, the P-113-DA peptide AKRHHGYKRKFH-D-3,4-dihydroxyphenethylamine (SEQ ID NO:6) includes a linker (e.g., Aspartic acid (D)) between the antimicrobial domain and dopamine (DA) domain. In some forms, the antimicrobial domain and phosphoserine domain are fused via any appropriate linker known in the art. Generally, such linkers have no specific biological activity other than to join or to preserve some minimum distance or other spatial relationship between the domains. The linker may be as simple as a covalent bond (e.g., a carbon-carbon bond, disulfide bond, carbon-heteroatom bond, etc.), or it may be a polymeric linker many atoms in length. The linker can be an organic molecule, group, polymer, or chemical moiety. In some forms, the linker is a carbon-nitrogen bond of an amide linkage. In some forms, the linker is a cyclic or acyclic, substituted or unsubstituted, branched or unbranched aliphatic or heteroaliphatic linker. The linker can be a single amino acid (e.g., Aspartic acid (D) or any other amino acid) or a plurality of amino acids. Linker sequences adopt a flexible extended conformation and do not exhibit a propensity for developing an ordered secondary structure. Preferably, the linker contains amino acids. Typical amino acids in flexible linkers include Gly (G), Asn (N) and Ser (S).

In some forms, the antimicrobial domain and phosphoserine domain forming the isolated peptide are fused via a linker that includes from about 1-20 amino acids, inclusive. In some forms, the linker includes from 1-5, 1-10, 1-15, or 1-20 amino acids.

The isolated peptide can be of any length or size, as long as it retains functionality (e.g., binding to tooth enamel, anti-biofouling and mineralizing abilities). In some forms, the peptide can have a length of up to 30 residues. For example, the peptide can have a length of about 6-30 residues, such as about 6-20 residues, about 10-15, or about 20-30 residues. In particular forms, the peptide has a length of 10, 11, 12, 13, 14, 15, or 20 residues. In some preferred forms, the peptide has a length of 12-14 residues.

Suitable peptides also include variants of the disclosed peptides, such as the peptide of SEQ ID NO:4, and modifications thereof retaining the same functional activity. For example, suitable peptides can include one or more point mutations or substitutions (e.g., 1, 2, 3, 4, 5 or more mutations) at any amino acid residue of SEQ ID NO: 4. The one or more substitutions can be conservative or non-conservative. For example, the peptide AKRHHGYKRKFH-SpSp (SEQ ID NO:4), can be modified by substituting one or more of the non-polar amino acid residues (A, G), with another, similarly non-polar residue, such as I or L. Alanine scanning of peptides is useful for identifying amino acids that can be modified without reducing binding or other properties of the peptide.

The term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical, but in all cases retain the same functional activity or mechanism of action. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5);

methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity. The following hydrophilicity values can be assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, and size. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of the peptides can include variants having about 50%, 60%, 70%, 80%, 90%, 95%, 96%, 97%, 98%, 99%, or more sequence identity to the peptide of interest. The term "conservative amino acid substitution", is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

B. Peptide Modifications

The disclosed peptides may be modified in various ways. In some forms, the modification(s) may render the peptides more stable (e.g., resistant to degradation in vivo) or confer other desirable characteristics as will be appreciated by one skilled in the art. Such modifications include, without limitation, chemical modification, N terminus modification, C terminus modification, peptide bond modification, backbone modifications, residue modification, D-amino acids, or non-natural amino acids or others. In some forms, one or more modifications may be used simultaneously. In preferred forms, the peptides are stabilized against proteolysis. For example, the stability and activity of peptides can be improved by protecting some of the peptide bonds with N-methylation or C-methylation. It is believed that modifications, such as amidation, also enhance the stability of peptides to peptidases.

Modifications to the peptides generally should leave them functional. It is understood that there are numerous amino acid analogs which can be incorporated into the peptides. For example, there are numerous D amino acids or other non-natural amino acids which can be used. The opposite stereoisomers of naturally occurring peptides are disclosed, as well as the stereo isomers of peptide analogs. Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

Either or both ends of a given linear peptide can be modified. For example, the peptides can be acetylated and/or amidated.

The peptides may contain naturally occurring α-amino acid residues, non-naturally occurring α-amino acid residues, and combinations thereof. The D-enantiomer ("D-α-amino acid") of residues may also be used. Incorporation of artificial amino acids such as beta or gamma amino acids and those containing non-natural side chains, and/or other similar monomers such as hydroxyacids are also contemplated, with the effect that the corresponding component is peptide-like in this respect.

Non-naturally occurring amino acids are not found or have not been found in nature, but they can by synthesized and incorporated into a peptide chain. Non-limiting examples of suitable non-natural amino acids (in L- or D-configuration) are azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, and 3-(6-chloroindolyl) alanin.

In some forms, peptide bonds (—CO—NH—) within the peptide may be substituted, for example, by N-methylated bonds (—N($CH_3$)—CO—), ester bonds (—C(R)H—C-0-0-C(R)—N—), ketomethylen bonds (—CO—$CH_2$—), CC-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH═CH—), retro amide bonds (—NH—CO—), peptide derivatives (—N(R)—$CH_2$—CO—), wherein R is the normal side chain, naturally presented on the carbon atom. These modifications can occur at any of the bonds along the peptide chain and even at several (e.g., 2, 3, 4 or more) at the same time.

The peptides can be utilized in a linear form, although it will be appreciated that in cases where cyclization does not severely interfere with peptide characteristics, cyclic forms of the peptides can also be used. For example, in some forms, an isolated P-113-DPS peptide (AKRHHGYKRKFH-SpSp; SEQ ID NO:4) can be in a cyclic form because of intramolecular bonds, and its conformation can change upon adsorption onto a tooth surface (see FIG. 12). As used herein in reference to a peptide, the term "cyclic" means a structure including an intramolecular bond between two non-adjacent amino acids or amino acid analogues. The cyclization can be effected through a covalent or non-covalent bond. A preferred method of cyclization is through formation of a disulfide bond between the side-chains of non-adjacent amino acids or amino acid analogs. A peptide also can cyclize, for example, via a lactam bond, which can utilize a side-chain group of one amino acid or analog thereof to form a covalent attachment to the N-terminal amine of the amino-terminal residue. Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

Peptidomimetics may optionally be used to inhibit degradation of the peptides by enzymatic or other degradative processes. The peptidomimetics can be produced by organic synthetic techniques. Non-limiting examples of suitable peptidomimetics include D amino acids of the corresponding L amino acids. D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides as long as activity is preserved.

C. Formulations and Devices

The disclosed peptides can be combined with a pharmaceutically acceptable carrier or excipient to form a pharmacological composition. For example, pharmaceutical compositions including an effective amount of the peptide or a plurality of copies of the peptide and a pharmaceutically acceptable excipient are provided. Typically, the excipient is suitable for administration to oral cavity. Pharmaceutically acceptable carriers can contain one or more physiologically acceptable compound(s) that act, for example, to stabilize the composition or to increase or decrease the absorption of the peptide(s). Suitable carriers, diluents and their formulations are described in *Remington: The Science and Practice of Pharmacy* (19th ed.) ed. A. R. Gennaro, Mack Publishing Company, Easton, PA 1995. Those of skill in the art can readily determine the various parameters for preparing and formulating the compositions without resort to undue experimentation. Physiologically acceptable compounds can include, for example, carbohydrates, such as glucose, sucrose, or dextrans, antioxidants, such as ascorbic acid or glutathione, chelating agents, low molecular weight proteins, protection enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like. Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain forms, the excipients are sterile and generally free of undesirable matter. These compositions can be sterilized by conventional, well-known sterilization techniques. For various oral dosage form excipients such as tablets and capsules sterility is not required.

In some forms, the peptides are formulated into pharmaceutical compositions for local administration. In preferred forms, pharmaceutical compositions of the peptides may be for topical administration, such as, to the oral cavity or mucosa, including tooth surfaces.

The peptides may be used in oral care products, which may have any suitable physical form, such as powder, paste, gel, liquid, ointment, or tablet. Exemplary oral care products include, but are not limited to, toothpaste, dental cream, gel or tooth powder, mouthwash, breath freshener, oral sprays, rinses, gargles, gums, tablets, oral lozenges, tooth whitening strips or solutions, cleaning solutions, toothpicks, toothbrushes, dental floss, varnish, and restorative materials, including, but not limited to, composite resin. Typically, the oral care products contain an effective amount of the peptides in an orally acceptable carrier. An effective amount of a peptide for use in an oral care product may vary depending on the type of product. Typically, the effective amount of the peptides is a proportion from about 0.001% to about 90% by weight of the total product composition. The oral care product may contain one type of peptide or a mixture of different peptides (e.g., of different sequence and/or length).

Components of an orally acceptable carrier are described in U.S. Pat. Nos. 6,740,311; 6,706,256; and 6,264,925; all of which are incorporated herein by reference. For example, in addition to the peptides, the oral care products may contain one or more of the following: abrasives, surfactants, chelating agents, fluoride sources, thickening agents, buffering agents, solvents, humectants, carriers, bulking agents, and additional oral benefit agents, as given above. Oral care products may be prepared using standard techniques that are well known in the art. If a composition contains more than one phase, typically, the different phases are prepared separately, with material of similar phase partitioning being added in any order. The two phases are combined using vigorous mixing to form the multiphase system (e.g., an emulsion or dispersion).

In some forms, the peptides are incorporated into oral care formulations, e.g., a prescription or over the counter product for use in a home, for travel, at work, in a dental office, at a hospital, etc. Such formulations include, but are not limited to toothpastes, mouthwashes, tooth whitening strips or solutions, cleaning solutions, dental floss, toothpicks, toothbrushes, oral sprays, oral lozenges, and the like.

The formulation of such oral care products is well known to those of skill, and the disclosed peptides can simply be added to such formulations in an effective dose (e.g., a prophylactic dose to inhibit dental carie formation, etc.). For example, toothpaste formulations are well known to those of skill in the art. Typically such formulations are mixtures of abrasives and surfactants; anticaries agents, such as fluoride; tartar control ingredients, such as tetrasodium pyrophosphate and methyl vinyl ether/maleic anhydride copolymer; pH buffers; humectants, to prevent dry-out and increase the pleasant mouth feel; and binders, to provide consistency and shape. Binders keep the solid phase properly suspended in the liquid phase to prevent separation of the liquid phase out of the toothpaste. They also provide body to the dentifrice, especially after extrusion from the tube onto the toothbrush.

In preparing toothpastes or gels, a thickening material can be added to provide a desirable consistency of the composition, to provide desirable active release characteristics upon use, to provide shelf stability, and to provide stability of the composition, etc. Exemplary thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Mouthwash formulations are also well known to those of skill in the art. For example, mouthwashes containing sodium fluoride are disclosed in U.S. Pat. Nos. 2,913,373, 3,975,514, and 4,548,809, and in US Patent Publications US 2003/0124068, US 2007/0154410. Mouthwashes containing various alkali metal compounds are also known: sodium benzoate (WO 94/09752); alkali metal hypohalite; chlorine dioxide (CN 1222345); alkali metal phosphate (US 2001/0002252, US 2003/0007937); hydrogen sulfate/carbonate (JP 8113519); cetylpyridium chloride (CPC) (see, e.g., U.S. Pat. Nos. 6,117,417, 5,948,390, and JP 2004051511). Mouthwashes containing higher alcohol (see, e.g., US 2002/0064505, US 2003/0175216); hydrogen peroxide (see, e.g., CN 1385145); $CO_2$ gas bubbles (see, e.g., JP 1275521 and JP 2157215) are also known. In some forms, these and other mouthwash formulations can further include one or more of the disclosed peptides.

Oral sprays, oral rinses, oral cleaning solutions, oral lozenges, gums, tablets, gargles, dental creams, and devices or instruments such as toothbrushes, toothpicks, dental floss, tooth whitening strips, and the like are also well known to those of skill in the art and can readily be adapted to incorporate the disclosed peptides. For example, the peptides can be incorporated onto the bristles of a toothbrush, or as a coating on dental floss or toothpicks. Suitable lozenge and chewing gum components are disclosed in U.S. Pat. No. 4,083,955.

In some forms, the oral care compositions include a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, can be present in a concentration from about 0% to about 70%, preferably from about 5% to about 25%, by weight of the compositions. Suitable humectants include edible polyhydric alcohols such as glycerin, sorbitol, xylitol, butylene glycol, polyethylene glycol, and propylene glycol, especially sorbitol and glycerin.

Flavoring and sweetening agents can also be included in the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition. Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition, coolants, salivating agents, warming agents, and numbing agents can be used as optional ingredients in compositions. These agents are present in the compositions at a level of from about 0.001% to about 10%, preferably from about 0.1% to about 1%, by weight of the composition. The coolant can be any of a wide variety of materials. Included among such materials are carboxamides, menthol, ketals, diols, and mixtures thereof.

The pH of the compositions can be adjusted through the use of buffering agents. In some forms, buffering agents can be used to adjust the pH of the compositions to a range of about 4.5 to about 9.5. Buffering agents include monosodium phosphate, trisodium phosphate, sodium hydroxide, sodium carbonate, sodium acid pyrophosphate, citric acid, and sodium citrate.

The foregoing oral care formulations and/or devices are meant to be illustrative and not limiting. Using the teaching provided herein, the peptides of the present invention can readily be incorporated into other products.

III. Methods of Manufacture

Methods of preparing the disclosed peptides and compositions thereof are described. In some forms, the peptides can be obtained commercially, such as from a vendor which provides custom peptide synthesis services. In some forms, peptides having a desired sequence can be synthesized or produced recombinantly. Thus, methods of making the peptides using known techniques are provided.

In some forms, the peptides can be produced by recombinant means (e.g., in bacteria, yeast, fungi, insect, vertebrate or mammalian cells) by methods well known to those skilled in the art. Generally this involves creating a DNA sequence that encodes the desired peptide, placing the DNA in an expression cassette under the control of a particular promoter, expressing the peptide in a host, isolating and/or purifying the expressed peptide and, if required, renaturing the peptide.

DNA encoding the peptide(s) can be prepared by any suitable method as described above, including, for example, cloning and restriction of appropriate sequences or direct chemical synthesis. The nucleic acid can be easily ligated into an appropriate vector containing appropriate expression control sequences (e.g. promoter, enhancer, etc.), and, optionally, containing one or more selectable markers (e.g. antibiotic resistance genes). The nucleic acid sequences encoding the peptides can be expressed in a variety of host cells, including, but not limited to, *E. coli*, other bacterial hosts, yeast, fungus, and various higher eukaryotic cells such as insect cells (e.g. SF3), the COS, CHO and HeLa cells lines, and myeloma cell lines. Once expressed, the recombinant peptide(s) can be purified according to standard procedures of the art, including ammonium sulfate precipitation, affinity columns, column chromatography, gel electrophoresis and the like.

In certain forms, the peptides are chemically synthesized by any of a number of fluid or solid phase peptide synthesis techniques known to those of skill in the art. For example, standard FMOC synthesis is described in the literature (e.g., solid phase peptide synthesis, see E. Atherton, RC Sheppard, Oxford University press (1989), or liquid phase synthesis (where peptides are assembled using a mixed strategy by BOC chemistry and fragment condensation). Solid phase synthesis in which the C-terminal amino acid of the sequence is attached to an insoluble support followed by sequential addition of the remaining amino acids in the sequence is a preferred method for the chemical synthesis of the peptides. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc, 85: 2149-2156, and Stewart et al. (1984) Solid Phase Peptide Synthesis, 2nd ed. Pierce Chem. Co., Rockford, 111.

Such methods include bench scale solid phase synthesis and automated peptide synthesis in any one of the many commercially available peptide synthesizers. Solid phase synthesis is commonly used and various commercial synthesizers are available, for example automated synthesizers by Applied Biosystems Inc., Foster City, CA; Beckman; MultiSyntech, Bochum, Germany etc. Solution phase synthetic methods may also be used, although this can be less convenient. Functional groups for conjugating the peptide to small molecules, label moieties, peptides, or proteins may be introduced into the molecule during chemical synthesis. In addition, small molecules and label moieties/reporter units may be attached during the synthetic process. Preferably, introduction of the functional groups and conjugation to other molecules minimally affects the structure and function of the subject peptide.

The peptides can be produced by stepwise synthesis or by synthesis of a series of fragments that can be coupled by well-known techniques. Chemical synthesis typically starts from the C-terminus, to which amino acids are sequentially added using either a Rink amide resin (resulting in an —$NH_2$ group at the C-terminus of the peptide after cleavage from the resin), or a Wang resin (resulting in an —OH group at the C-terminus). Accordingly, peptides having a C-terminal moiety that may be selected from the group consisting of —H, —OH, —COOH, —$CONH_2$, and —$NH_2$ are contemplated for use.

Standard Fmoc (9-florenylmethoxycarbonyl) derivatives include Fmoc-Asp(OtBu)—OH, Fmoc-Arg (Pbf)-OH, and Fmoc-Ala-OH. Couplings are mediated with DIC (diisopropylcarbodiimide)/6-Cl-HOBT (6-chloro-1-hydroxybenzotriazole). In some embodiments, the last four residues of the peptide require one or more recoupling procedures. In particular, the final Fmoc-Arg(Pbf)-OH coupling can require recoupling. For example, a second or third recoupling can be carried out to complete the peptide using stronger activation chemistry such as DIC/HOAT (1-hydroxy-7-azabenzotriazole) or HATU (1-[bis(dimethylamino)methylene]-1H-1,2,3-triazolo[4,5-b]pyridinium 3-oxid hexafluorophosphate)/NMM (N-methylmorpholine).

Acidolytic cleavage of the peptide can be carried out with the use of carbocation scavengers (thioanisole, anisole and $H_2O$). Optimization can be achieved by varying the ratio of the components of the cleavage mixture. An exemplary cleavage mixture ratio is 90:2.5:2.5:5 (TFA-thioanisole-anisole-$H_2O$). The reaction can be carried out for 4 hours at room temperature. In some forms, the removal of residual impurities is carried out by wash steps. For example, trifluoroacetic acid (TFA) and organic impurities can be eliminated by precipitation and repeated washes with cold diethyl ether and methyl t-butyl ether (MTBE).

Peptides produced using the disclosed methods can be purified using high pressure liquid chromatography (HPLC). Suitable solvents for dissolving the peptides include neat TFA. Typically, the peptides remain soluble at TFA concentrations of 0.5% to 8% and can be loaded onto reverse phase (RP)-HPLC columns for salt exchange. Exemplary salt exchange methods use 3-4 column volumes of acidic buffer to wash away the TFA counter ion due to its stronger acidity coefficient. Buffers suitable for use in washing away the TFA counter ion include 0.1% HCl in $H_2O$.

Following removal of TFA, peptides can be eluted with a step gradient. Exemplary elution buffers include 30% acetonitrile (MeCN) vs. 0.1% HCl in $H_2O$. For acetate exchange, peptides can be loaded from the same diluted TFA solution, washed with 3-4 column volumes of 1% acetic acid (AcOH) in $H_2O$, followed by 2 column volumes of 0.1 M $NH_4OAc$ in $H_2O$, pH 4.4. In some embodiments, the column is washed again with 3-4 column volumes of 1% AcOH in $H_2O$.

Analytical HPLC can be carried out to assess the purity and homogeneity of peptides. An exemplary HPLC column for use in analytical HPLC is a PHENOMENEX® JUPITER® column. A step gradient can be used to separate the peptide composition. In some embodiments, the gradient is from 1%-40% MeCN vs 0.05% TFA in $H_2O$. The change in gradient can be achieved over 20 minutes using a flow rate of 1 ml/min. Peptides can be detected using UV detection at 215 nm.

Where the peptides or compositions thereof are required to be sterilized or otherwise processed for the removal of undesirable contaminants and/or microorganisms, filtration can be used. Filtration can be achieved using any system or procedures known in the art. In some forms, filtration removes contaminants or prevents the growth or presence of microorganisms. Exemplary microorganisms and contaminants that can be removed include bacteria, cells, protozoa, viruses, fungi, and combinations thereof. In some forms, the step of filtration is carried out to remove aggregated or oligomerized peptides. For example, solutions of the peptides can be filtered to remove oligomers on the basis of size.

IV. Methods of Use

Disclosed herein are various methods related to the disclosed peptides and compositions and their use. The peptides and compositions thereof can be used in therapeutic and/or prophylactic applications. For example, disclosed are methods of using the peptides and compositions thereof to reduce or prevent tooth decay, repair tooth decay, reduce or prevent enamel demineralization, promote enamel mineralization, or combinations thereof.

The peptides can be incorporated into or onto an oral care composition or device. An "oral care composition" is any composition that is suitable for administration or application to the oral cavity of a human or animal subject for enhancing the health, hygiene or appearance of the subject, for example, providing benefits such as: the prevention or treatment of a condition or disorder of the teeth, gums, mucosa or other hard or soft tissue of the oral cavity; the provision of sensory, decorative or cosmetic benefits; and combinations thereof. Typically, the oral care composition, in the ordinary course of usage, is not intentionally swallowed for purposes of systemic administration, but is rather retained in the oral cavity for a time sufficient to contact substantially all of the dental surfaces and/or oral tissues for purposes of oral activity. The oral composition may be a single phase oral composition or may be a combination of two or more oral compositions. Exemplary oral care compositions or devices include, without limitation, mouthwashes, toothpastes, dental creams, oral sprays, rinses, gargles, gums, tablets, oral lozenges, dental floss, tooth whitening strips or solutions, cleaning solutions, toothpicks, and toothbrushes.

For example, in some forms, the peptides can be incorporated into toothpaste or mouthwash to reduce or prevent colonization or recolonization of the oral cavity and thereby reduce the incidence and/or degree of dental carie formation. In various forms, the peptides can be incorporated into dental floss for similar purposes or can be provided in swabs that are used to swab the teeth and oral mucosa.

In some forms, the peptides and compositions thereof are administered locally. In some forms, the peptides and compositions thereof are administered topically, e.g., applied to the oral cavity.

The peptides and compositions thereof can be used therapeutically and/or prophylactically. For example, in some forms, subject administered the peptides and compositions thereof suffers from an infection or is at risk for infection (e.g., pathogenic bacterial infection in the mouth). In some forms, the subject administered the peptides and compositions thereof suffers from dental caries or is at risk for developing dental caries.

The peptides and compositions thereof can be used in methods to treat and/or prevent dental caries or other pathologies of the teeth or oral mucosa. In some forms, the peptides and compositions thereof are used in methods to repair tooth decay (e.g., promote mineralization of a tooth surface, such as enamel). In some forms, the peptides and compositions thereof are used in methods to reduce or prevent tooth surface (e.g., enamel) demineralization. In some forms, the peptides and compositions thereof are used in methods to reduce or prevent adhesion of microorganisms (e.g., bacteria) to the tooth surface. In some forms, the peptides and compositions thereof are used in methods to reduce or prevent formation of biofilms on the tooth surface. In some forms, the peptides and compositions thereof are used in methods to reduce or prevent dental plaque formation. In some forms, the peptides and compositions thereof are used in methods to inhibit growth and/or proliferation bacteria in the oral cavity (e.g., caries-causing bacteria such as *S. mutans*). In some forms, the peptides and compositions thereof are used in methods to kill bacteria in the oral cavity (e.g., caries-causing bacteria such as *S. mutans*). The methods can also include cleaning and polishing teeth and reducing the incidence of stain, plaque, gingivitis and calculus on dental enamel. In certain forms, the method includes a combination of the foregoing.

It is understood that any of the foregoing methods can include administering or applying the peptides and compositions thereof to the subject though not explicitly recited. Thus, an exemplary method involves applying a disclosed oral care composition or device containing the peptides to the teeth and/or oral cavity of a subject. For example, a composition containing the peptides can be brushed, sprayed, or otherwise coated onto the teeth. In some forms, a composition containing the peptides is applied to the oral cavity by gargling, rinsing or shaking.

In some forms, the methods involve contacting a subject's dental enamel surfaces and/or oral mucosa with the oral care compositions. This can be accomplished by brushing, rinsing (e.g., with a slurry or mouthwash or rinse). Other methods include contacting a topical oral gel, paste, mouthspray, or other form with the subject's teeth and/or oral mucosa.

In some preferred forms, a method of reducing or preventing and/or repairing tooth decay in a subject in need thereof includes contacting the subject's teeth and/or oral cavity with a peptide having the sequence AKRHHGYKRKFH-SpSp (SEQ ID NO:4) or a sequence having at least 90% sequence identity to AKRHHGYKRKFH-SpSp (SEQ ID NO: 4). In some preferred forms, a method of reducing or preventing enamel demineralization and/or promoting enamel mineralization in a subject in need thereof includes contacting the subject's teeth and/or oral cavity with a peptide having the sequence AKRHHGYKRKFH-SpSp (SEQ ID NO:4) or a sequence having at least 90% sequence identity to AKRHHGYKRKFH-SpSp (SEQ ID NO:4).

The subject may be any human or lower animal. For example, the subject can be a household pet or other domestic animals, or animals kept in captivity. For example, a method of use may include brushing a dog's teeth with one of the disclosed toothpastes, toothbrushes, or other compositions or devices. Another example would include the rinsing of a cat's mouth with an oral composition for a sufficient amount of time to see a benefit. Pet care products such as chews and toys may be formulated to contain the oral care compositions. The composition including the peptides can be incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

Preferably, the subject is a human.

Effective Amounts

Typically, the methods involve administering or applying an effective amount of the peptides or compositions thereof. For example, in some embodiments, the peptide compositions are administered to a subject in an effective amount for treatment and/or prevention of a disease, disorder or condition (e.g., dental caries or other pathologies of the teeth or oral mucosa).

The effective amount can be a dosage sufficient to treat, inhibit, or alleviate one or more symptoms of a disorder, disorder or condition being treated or to otherwise provide a desired pharmacologic and/or physiologic effect. The effective amount of the peptide compositions will vary from subject to subject, and can depend on the species, age, weight and general condition of the subject, the severity of the disorder being treated, and its mode of administration. Thus, it is not possible to specify an exact amount for every therapeutic composition. However, an appropriate amount can be determined by one of ordinary skill in the art using only routine experimentation given the teachings herein. For example, effective dosages and schedules for administering the therapeutics may be determined empirically, and making such determinations is within the skill in the art. The dosage ranges for the administration of the compositions are those large enough to effect one or more desired responses.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage can depend upon the age, condition, and sex of the subject, the desired therapeutic effect, on the route of administration, and on the duration of the treatment desired. It will also be appreciated that the effective dosage of the composition used for treatment may increase or decrease over the course of a particular treatment.

The concentration of peptides in the compositions or the total amounts can vary widely, and will be selected primarily based on activity of the particular peptide(s) and/or composition thereof, particular mode of administration selected, and the subject's needs. Typical dosages range from about 1 μM mol$-^1$ to 100 μM mol$-^1$. For example, in some forms, the concentration of peptide(s) is in the range of about 5-10 μM mol$-^1$, 10-50 μM mol$-^1$, 20-60 μM mol$-^1$, 30-70 μM mol$-^1$, 40-80 μM mol$-^1$, or 50-100 μM mol$-^1$. In some forms, the concentration of peptide(s) is about 5, 10, 20, 30, 40, 50, 60, 70, 80, 90, or 100 μM mol$-^1$. In particular forms, the concentration of peptide(s) is about 8 μM mol$-^1$ or 64 μM mol$-^1$.

In some forms, the peptides are in an amount effective to reduce or prevent tooth decay, reduce or prevent bacterial biofilm formation, reduce or prevent dental plaque formation, reduce or prevent bacterial adhesion to tooth surfaces, inhibit growth and/or proliferation of oral bacteria, induce or increase enamel mineralization, or combinations thereof.

The mouth is colonized by 200 to 300 bacterial species, but only a limited number of these species participate in dental decay (caries) or periodontal disease. The tooth surface normally loses some tooth mineral from the action of the acid formed by plaque bacteria after ingestion of foods containing fermentable carbohydrates. This mineral is normally replenished by the saliva between meals. However, when fermentable foods are eaten frequently, the low pH in the plaque is sustained and a net loss of mineral from the tooth occurs. This low pH selects for aciduric organisms, such as *S. mutans* and lactobacilli, which store polysaccharide and continue to secrete acid long after the food has been swallowed. Reports indicate that bacterial species such as species of the genera *Veillonella, Lactobacillus, Bifidobacterium*, and *Propionibacterium*, low-pH non-*S. mutans* streptococci, *Actinomyces* spp., and *Atopobium* spp., likely play important roles in caries progression (Aas J A., et al., J Clin Microbiol., 46(4):1407-1417 (2008)).

Thus, in some forms, the bacteria contained in the biofilm and/or dental plaque, the bacteria whose adhesion is reduced or prevented, and/or whose growth and/or proliferation is inhibited is bacteria present in the oral cavity such as species of the genera *Streptococcus, Veillonella, Lactobacillus, Bifidobacterium*, and *Propionibacterium*. In some forms, the bacteria contained in the biofilm and/or dental plaque, the bacteria whose adhesion is reduced or prevented, and/or whose growth and/or proliferation is inhibited is gram positive bacteria.

In some forms, the bacteria contained in the biofilm and/or dental plaque, the bacteria whose adhesion is reduced or prevented, and/or whose growth and/or proliferation is inhibited is acidophilic bacteria or acid-producing bacteria.

In any of the foregoing, the bacteria can be selected from *S. mutans, S. faecalis, S. parasanguinis, S. salivarius, S. sobrinus, L. acidophilus, L. casei, Actinomyces* spp., *Atopobium* spp., *Corynebacterium* sp., *Leptotrichia* sp., *A. gerencseriae*, and combinations thereof.

Timing of Administration and Regimens

Dosages and timing of administration can vary. Guidance can be found in the literature for appropriate dosages for given classes of pharmaceutical products. Persons of ordinary skill can determine optimum dosages, dosing methodologies and repetition rates. Optimum dosages may vary depending on the relative potency of individual therapeutics, and can generally be estimated based on $EC_{50}$s, minimal bactericidal concentrations (MBC), and/or minimum inhibitory concentrations (MIC) found to be effective in in vitro and in vivo animal models.

Administration of the peptides and compositions thereof can be continued for an amount of time sufficient to achieve one or more desired goals (e.g., therapeutic or prophylactic goals). Treatment can be continued for a desired period of time, and the progression of treatment can be monitored using any suitable means known in the art. In some forms, administration is carried out every day of treatment (e.g., multiple times a day), or every week, or every fraction of a week. In some forms, administration regimens are carried out over the course of up to two, three, four or five days, weeks, or months, or for up to 6 months, or for more than 6 months, for example, up to one or two years.

Single or multiple administrations of the compositions may be administered depending on the dosage and frequency as required and tolerated by the subject. In any event, the composition should provide a sufficient quantity of the peptides to effect the desired outcome. In some forms, the multiple doses of the compositions are administered before an improvement in disease condition is evident. For example, in some forms, the subject receives the composition, over a period of 1, 2, 3, 4, 5, 6 7, 14, 21, 28, 35, or 48 days or weeks before an improvement in the disease or condition is evident.

In some forms, the composition is administered or applied for a time of from about 30 seconds to about 30 minutes, for example about 30 seconds, about 1, 2, 3, 4, 5, 6, 7, 8, 9, 10, 11, 12, 13, 14, 15, 16, 17, 18, 19, 20, 25, or 30 minutes. In some forms the composition is administered or applied one or more times per day, e.g., 1, 2, 3 or more times per day.

V. Kits

The disclosed reagents, materials, and compositions as well as other materials can be packaged together in any suitable combination as a kit useful for performing, or aiding in the performance of, the disclosed methods. It is useful if the components in a given kit are designed and adapted for use together in the disclosed method.

In some forms, the kits can include, for example, a composition or device containing one or more disclosed peptides. The kits typically include a container containing one or more of the active agents (e.g., the disclosed peptides) described herein. In certain forms, the active agent(s) can be provided in a unit dosage formulation (e.g., suppository, tablet, cap let, patch, etc.) and/or may be optionally combined with one or more pharmaceutically acceptable excipients. In particular forms, the kits include one or more oral care compositions or devices such as a toothpaste, mouthwash, toothpick, dental floss, gum, gel, or combinations thereof.

Preferably, the kits include instructional material. The instructional material can include a publication, a recording, a diagram, or any other medium of expression which can be used to communicate the usefulness of the compositions and methods of the kit. For example, the instructional material may provide instructions for methods using the kit components, such as performing oral rinses, oral gargles, teeth cleaning, teeth whitening, and the like.

The present invention will be further understood by reference to the following non-limiting examples.

EXAMPLES

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

Example 1: P-113-DPS Exhibits Antibacterial and Remineralizing Properties

Materials and Methods

Synthesis of Bioactive Peptides

Five bioactive peptides including P-113 (AKRHHGYKRKFH; SEQ ID NO:2), P-113-DPS (AKRHHGYKRKFH-SpSp; SEQ ID NO:4), P-113-DA (AKRHHGYKRKFH-D-3,4-dihydroxyphenethylamine; SEQ ID NO:6), P-113-SK (AKRHHGYKRKFH-SKHKGGKHKGGKHKG; SEQ ID NO:5), and Sp-H5 (phosphoserine-DSHAKRHHGYKRKFHEKHHSHRGY; SEQ ID NO:7) were synthesized by Shanghai Science Peptide Biological Technology Co., LTD (Shanghai, China) using the standard 9-fluorenylmethoxycarbonyl (FMOC) solid-phase method. Sequence purity (>95%) and authenticity were determined by analytical reverse-phase high-performance liquid chromatography (HPLC). The molecular mass was determined by mass spectrometry (MS). Peptides were lyophilized for storage at −70° C. and dissolved in 10 mM 4-(2-hydroxyethyl)-1-piperazineeth anesulfonic acid (HEPES) buffer at pH 7 prior to use.

Bacterial Strains and Growth Media

*Streptococcus mutans* (ATCC 35668, ATCC, Manassas, USA) were cultured in Horse Blood Medium under anaerobic (85% $N_2$, 10% $H_2$, and 5% $CO_2$) conditions at 37° C. Cells were harvested by centrifugation (5000 rpm, 10 min), washed once with 10 mM sodium phosphate-buffered saline (PBS, pH 7.2), and resuspended in brain-heart infusion broth (BHI, Difco Laboratories, Detroit, USA) at a concentration of $10^6$ CFU/mL.

Preparation of Tooth Slices

After approval from the Institutional Review Board of the University of Hong Kong/Hospital Authority Hong Kong West Cluster (IRB No: UW17-362), human third molars were collected from patients with written informed consent. 3×3×1.5 $mm^3$ (number: 197) tooth slices were prepared using a water-cooled diamond saw (IsoMet low-speed saw, Buehler, Lake Bluff, IL, USA). One working surface of complete enamel tissue from each tooth slice was generated using the MicroCT Skyscan 1172 (Bruker MicroCT, Kontich, Belgium). The enamel working side of the tooth slice was polished and other sides marked with acid-proof nail polish. All tooth slices were cleaned and stored in deionized water at 4° C.

Adsorption Capacity Assay

The adsorption of P-113, P-113-DPS, P-113-DA, and P-113-SK to HA particles (Sigma Chemical Co., St Louis, USA) was measured using the Micro BCA method with Sp-H5 as the control group. Solutions of P-113, P-113-DPS, P-113-DA, P-113-SK and Sp-H5 in 10 mM HEPES buffer (pH 7) were diluted to 10 nmol/mL concentrations, and 200 µL was placed into each tube (P-113, N=10; P-113-DPS, N=10; P-113-DA, N=10; P-113-SK, N=10; and Sp-H5, N=10). Peptide solutions were mixed with (n=5) or without (n=5) HA particles (20 mg/tube) in each group. Tubes were placed onto a rotator overnight at 37° C. for complete reaction. Tubes containing the peptide solution and HA were centrifuged (13000 rpm, 1 min) and the supernatant collected. Bovine serum albumin (BSA) standard solutions (working range=5-250 µg/mL) and working reagent were prepared using the Pierce BCA Protein Assay Kit (Rockford, IL, USA). Working reagents (100 µL/well) were added to a 96-well plate, followed by standard and peptide solutions (100 µL/well). The Plate was incubated in the dark for 30 min and the absorbance (562 nm) measured using a plate reader. The concentration (C) of the BSA standard solution was linear with the absorbance (A) at 562 nm. The function of C=a*A+b was determined (a and b as constants). The final concentration (the peptide solution mixed with HA) and the initial concentration (the peptide solution without HA) were computed using the function and the generated absorbance data of the peptide solution mixed with and without HA.

Adsorption Time Assay

The adsorption time of peptides to the tooth enamel was also tested using the Micro BCA method. Solutions of P-113, P-113-DPS, P-113-DA, and P-113-SK in 10 mM HEPES buffer (pH 7) were diluted to 10 nmol/mL. Enamel working surfaces of tooth slices (N=20) were exposed to P-113 solution (n=5), P-113-DPS solution (n=5), P-113-DA solution (n=5), and P-113-SK solution (n=5), respectively. The remaining extraneous surfaces were covered with wax. Tubes were placed into a rotator at 37° C. At t=0, 5, 20, 40, 60, and 120 min, 100 µL of peptide solution was removed and added to BSA standard solutions (100 µL/well) and working reagent (100 µL/well) in a 96-well plate. After a 30-min incubation, absorbance was measured. A function of C=a*A+b was determined (a and b are constants). The concentrations of the peptide solution at different time points (C0, C1, C2, C3, C4, and C5 at 0, 5, 20, 40, 60, and 120 min, respectively) were computed based on absorbances (A0, A1, A2, A3, and A4, respectively).

Anti-Planktonic Bacterial Ability

Two-fold serial dilutions (in 10 mM HEPES) of P-113, P-113-DPS, P-113-DA, P-113-SK, and Sp-H5 prepared in 25% BHI medium were pipetted into a 96-well cell culture plate at final concentrations from 0.125-128 µmol/mL [100 µL/well]. Each well was seeded with 10 µL bacterial suspension at a final concentration of $10^6$ CFU/mL. Sp-H5 with bacterial cells and 25% BHI medium with and without bacterial cells in 10 mM HEPES buffer (pH 7) were used as the positive, negative, and blank control group, respectively. After a 24-h incubation, absorbance was measured at 595 nm using a microplate reader to assess cell growth. The minimal inhibitory concentration (MIC) was defined as the lowest concentration of peptide resulting in at least 90% reduction in absorbance compared to the negative control group. The minimal bactericidal concentration (MBC) was defined as the lowest concentration of peptide resulting in no colony formation on agar plates after incubation. 10 µL of cell suspension from each well were plated on horse blood agar plates and incubated at 37° C. for 48 h. All determinations were conducted in triplicate experiments.

Anti-Biofilm Activity

*S. mutans* biofilms were cultured on enamel working surfaces in a 96-well plate. Tooth slices (N=32) were autoclave-sterilized prior to anti-biofilm activity testing. 200 µL *S. mutans* in BHI ($10^6$ CFU/mL) was added to each well. After a 24-h incubation at 37° C., each tooth slice was washed once with PBS. Tooth slices were incubated in a new 96-well plate at 32, 64, and 128 µmol/mL concentrations with P-113+BHI, P-113-DPS+BHI, P-113-DA+BHI, P-113-SK+BHI, Sp-H5+BHI, or BHI (control) in duplicate for 24 h at 37° C. (in 10 mM HEPES). After incubation, tooth slices were washed once with PBS. One tooth slice at random in each group was stained with the LIVE/DEAD BacLight Bacterial Viability Kit (L7012, Thermo Fisher Scientific, Waltham, USA) and incubated in the dark for 30 min.

Fluorescence images were obtained using confocal laser scanning microscopy (CLSM, Fluoview 1000, Olympus, USA). A separate tooth slice was used for the counting of colony-forming units (CFU). Tooth slices were placed in 1 mL BHI solution, and adherent biofilms were removed from the enamel surfaces by sonication for 30 sec. Ten-fold serial dilutions of the suspensions were plated in duplicate on horse blood agar. CFU's were counted after 48-h incubation. Three independent biofilm experiments were performed.

Anti-Bacterial Adhesion Ability

Tooth slices (N=32) were immersed in 8, 16, and 32, μmol/mL P-113, P-113-DPS, P-113-DA, P-113-SK, and Sp-H5 solutions (in 10 mM HEPES) or 10 mM HEPES buffer (control, 100 μL/well) in duplicate at 37° C. overnight. After overnight incubation, they were placed in a 96-well plate, followed by 200 μL *S. mutans* in BHI ($10^6$ CFU/mL) and incubation at 37° C. for 5 h. Tooth slices were washed once with PBS, one tooth slice at random from each group was stained, and fluorescence images obtained by CLSM. Separate tooth slices were used for CFU counting. Three independent biofilm experiments were performed.

Demineralization Assay

Tooth slices (N=30) were immersed in 8 μmol/mL P-113, P-113-DPS, P-113-DA, P-113-SK, Sp-H5 (n=5 for each) solutions (in 10 mM HEPES) or HEPES (control) overnight. Tooth slices were incubated in 2 mL demineralization solution (2.2 mM $CaCl_2$, 2.2 mM $NaH_2PO_4$, 0.05 M acetic acid, pH 4.5) for 7 days at 37° C. Lesions depths were analyzed by MicroCT Skyscan 1172. Mineral calcium (Ca) or phosphorus (P) concentrations before and after immersion were measured using Inductively Coupled Plasma Optical Emission Spectrometer (ICP-OES; Spectro Arcos, Kleve, Germany). Ca/P loss was expressed as $mM/cm^2$. The mean values of Ca/P loss were analyzed for each group using ANOVA at the 1‰ significance level.

Remineralization Assay

The enamel working surface of tooth slices (N=30) was acid-etched in 37% phosphoric acid for 1 min and rinsed with deionized water for 1 min. The slices were immersed in 8 μmol/mL P-113, P-113-DPS, P-113-DA, P-113-SK, Sp-H5 (n=5 for each) solutions (in 10 mM HEPES) or HEPES (control) overnight. All tooth slices were incubated in 7 mL remineralization solution (2.58 mM $CaCl_2 \cdot 2H_2O$, 1.55 mM $KH_2PO_4$, 10 mg/L NaF, 180 mM NaCl, 50 mM Tris-HCl, pH 7.6) for 24 h. The enamel surface and cross-section morphology were analyzed by FE-SEM (Hitachi, S4800). Ca/P concentrations in the solutions before and after immersion were calculated by ICP-OES. The mean values for Ca/P gain were analyzed using ANOVA at the 1‰ significance level.

Cytocompatibility Test

The toxicity of peptides was tested using MC3T3-E1 cells (ATCC 2593, ATCC, Manassas, USA). MC3T3-E1 cells ($5\times10^3$) were seeded in a 96-well plate (N=72). After 24 h, cells were exposed to peptide solutions (P-113, P-113-DPS, P-113-DA, P-113-SK, or Sp-H5) for 24 h at four different concentrations: 4, 8, 16, and 32 μM $mol^{-1}$, in triplicate. Cells not exposed to peptides served as the control group. MC3T3-E1 cell proliferation after peptide exposure was evaluated using Cell Counting Kit-8 assay (CCK-8 assay, Sigma-Aldrich, USA).

Proliferation of MC3T3-E1 cells on peptide-coated enamel surface was tested. Tooth slices (N=48) were immersed in sterilized peptide solutions (8 μM $mol^{-1}$ P-113, P-113-DPS, P-113-DA, P-113-SK, or Sp-H5, n=8) or deionized water (control, n=8) for 30 min at 37° C. MC3T3-E1 cells ($5\times10^3$) were seeded onto the enamel working surfaces in a 96-well plate. After culturing for 1 and 3 days, three tooth slices in each group were used to test the proliferation of MC3T3-E1 cells by CCK-8 assay. The one tooth slice left in each group was stained by CellTracker Green (C7025, Thermo Fisher Scientific, USA). Fluorescence images were taken with CLSM.

Molecular Dynamics Analysis of Bioactive Peptides

Three systems were constructed using the software GROMACS 5.0.4: (1) peptide adsorption onto the HA system, (2) peptide-HA complexes in the demineralization system, and (3) peptide-HA complexes in the remineralization system. Peptide structures were simulated by Swiss-PdbViewer. The initial structures of the peptide molecules were built on the (010) surface of HA crystals. The 100-ns dynamic simulation was carried out for every system. When the reaction reached equilibrium, the adsorption mechanism and occupancy situation of peptides onto HA were analyzed. The demineralization system was introduced onto the peptide-HA complexes surface (after equilibrium of peptide adsorption onto HA) based on the ion ratio [acetate ions ($Ace^-$)/$Ca^{2+}$/phosphate ions ($PO_4^{3-}$)] in demineralization solution. Remineralization systems were built on the peptide-HA complex surface according to the ion ratio ($Ca^{2+}/PO_4^{3-}$) in the remineralization solution. Molecular dynamic reactions among ions, peptides, and HA were analyzed. Binding energy was used to analyze the reaction of peptides and ions, and HA and ions.

Statistical Analysis

Statistical analyses were performed using SPSS 26.0 software (IBM Corporation, Armonk, NY, USA). ANOVA was used to examine means with more than two groups, and Tukey HSD tests were used to test their mutual significance.

Results

Adsorption Evaluation

The adsorption amount of P-113, P-113-DPS, P-113-DA, P-113-SK, and Sp-H5 with HA particles is shown in Table 1. A linear function C=316.03A−17.302 (R=0.9996) was built. Using this function, initial and final concentrations of peptides mixed with HA particles were computed. Using one-way ANOVA, a significant difference was detected in the concentration change among groups (P<0.001). By Tukey HSD multiple comparisons, P-113-DPS exhibited stronger adsorption capacity with HA particles than Sp-H5 and all other solutions.

TABLE 1

Adsorption amount for the indicated peptides with HA Particles.

| Group | Initial concentration (Mean ± SD, nM $mL^{-1}$) | Final concentration (Mean ± SD, nM $mL^{-1}$) | Concentration change (95% CI) | p value | Multiple comparison (Concentration change) |
|---|---|---|---|---|---|
| P-113 | 10.15 ± 0.35 | 9.86 ± 0.23 | 0.29 (−0.01-0.61) [1] | <0.001 | [2] > [5] > [1] [2] > [4] > [3] |

TABLE 1-continued

Adsorption amount for the indicated peptides with HA Particles.

| Group | Initial concentration (Mean ± SD, nM $mL^{-1}$) | Final concentration (Mean ± SD, nM $mL^{-1}$) | Concentration change (95% CI) | p value | Multiple comparison (Concentration change) |
|---|---|---|---|---|---|
| P-113-DPS | 10.37 ± 0.36 | 6.56 ± 0.78 | 4.13 (3.28-4.88) [2] | | [1] = [3] [4] = [5] |
| P-113-DA | 10.28 ± 0.36 | 10.05 ± 0.99 | −0.17 (−0.55-0.40) [3] | | |
| P-113-SK | 10.32 ± 0.33 | 7.71 ± 0.39 | 2.61 (2.05-3.47) [4] | | |
| Sp-H5 | 10.00 ± 0.33 | 6.73 ± 0.12 | 3.27 (2.92-3.58) [5] | | |

Figure 3:
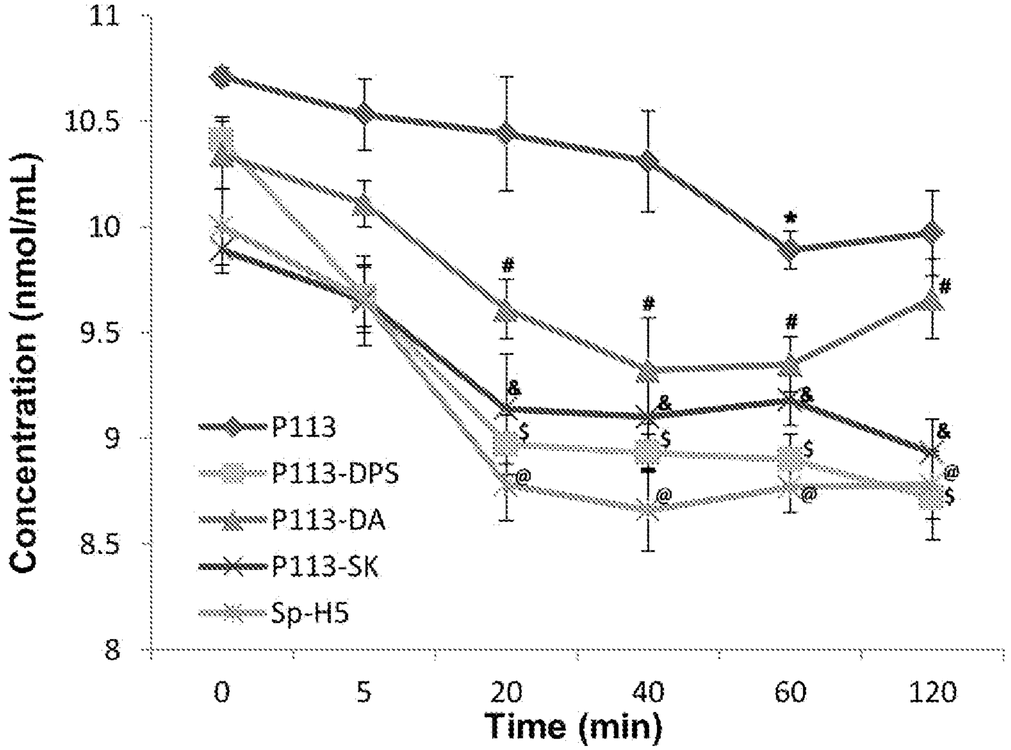
FIG. 3 is a graph showing adsorption time of P-113, P-113-DPS, P-113-DA, P-113-SK, and Sp-H5 on tooth enamel surfaces. Where indicated, a significant concentration difference was observed in the time point with an icon (*, #, &, $ and @, respectively, P<0.01) compared to the 0 min time point for the respective peptide.

The adsorption time of P-113, P-113-DPS, P-113-DA, P-113-SK, and Sp-H5 with enamel was also investigated (FIG. 3). The concentrations of peptide solutions at different time points (0, 5, 20, 40, 60 and 120 min) were calculated based on the linear function C=317.5A−21.406 (R=0.9987) using their absorbance values. By one-way ANOVA, a significant decrease in concentration was observed from 0 to 20 min in the P-113-DPS solution (P<0.01). There was no significant difference in concentration at 40, 60, and 120 min. The majority of adsorption reactions between P-113-DPS and enamel occurred within 20 minutes. P-113-DA, P-113-SK, and Sp-H5 had similar adsorption time curves. However, P-113 showed a slower adsorption reaction with a significant decrease in concentration at 60 minutes.

Anti-Biofouling Activity

The susceptibility assay for planktonic *S. mutans* in P-113, P-113-DPS, P-113-DA, P-113-SK, and Sp-H5 is summarized in Table 2. P-113-DPS showed the strongest anti-planktonic *S. mutans* activity based on the lowest MIC and MBC values in the group.

TABLE 2

MIC and MBC of the indicated peptides against *S. mutans*.

| Peptides | MIC (μM $mL^{-1}$) | MBC (μM $mL^{-1}$) |
|---|---|---|
| P-113 | 32 | >128 |
| P-113-DPS | 8 | 16 |
| P-113-DA | 16 | 32 |
| P-113-SK | 32 | 64 |
| Sp-H5 | 8 | 32 |

After 24 h of exposure of *S. mutans* biofilms to P-113, P-113-DPS, P-113-DA, P-113-SK, and Sp-H5 solutions with different concentrations, the majority of *S. mutans* were dead (data not shown) as determined by CLSM images of P-113-DPS and P-113-DA with concentrations of 64 and 128 μmol/mL. CLSM images of P-113-SK and Sp-H5 show similar results only at 128 μmol/mL (data not shown). In contrast, the majority of *S. mutans* in BHI and P-113 were alive. In addition, SEM imaging showed *S. mutans* cell membrane damage with various punctures as a result of incubation with P-113-DPS (data not shown).

Figure 4:
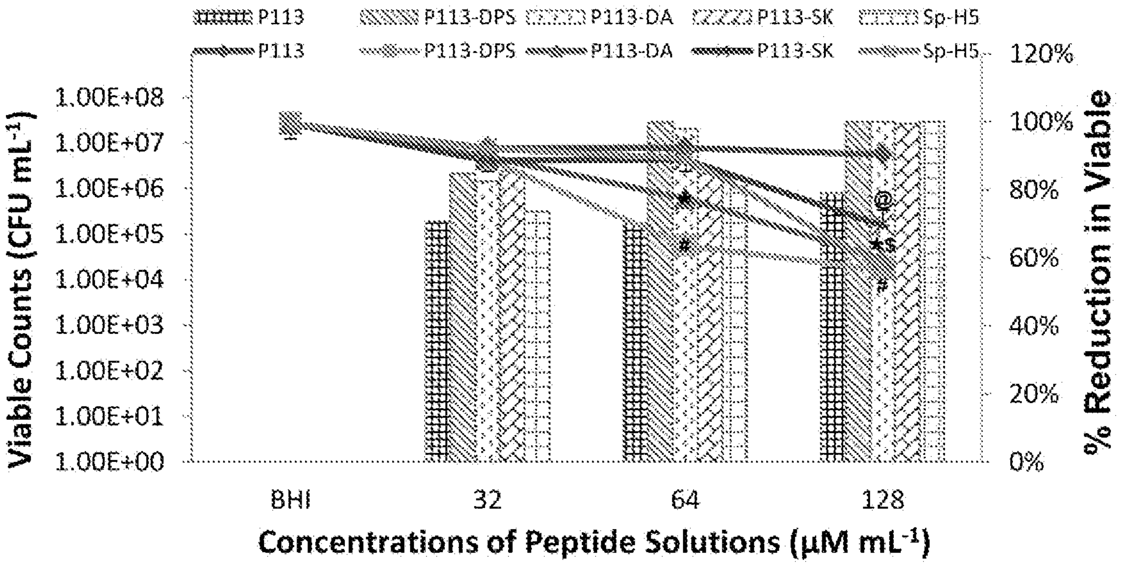
FIG. 4 is a graph showing viable counts (left ordinate and point plot) and percentage reduction of viability counts (right ordinate and bar chart) of *S. mutans* biofilms after 24 hours of exposure to BHI, P-113, P-113-DPS, P-113-DA, P-113-SK and Sp-H5 solutions at the indicated concentrations. The viable counts with an icon (*, #, $ or @) indicate a P<0.001, compared with BHI.

Approximately 99% *S. mutans* were killed by 64 μmol/mL P-113-DPS or P-113-DA, and 128 μmol/mL P-113-SK or Sp-H5 using quantitative approaches. In contrast, 79% *S. mutans* were killed by 128 μmol/mL P-113. Viability counts reduced significantly from 64 μmol/mL P-113-DPS [5.47E+04 (CFU/mL)] or P-113-DA [6.04E+05 (CFU/mL)], and 128 μmol/mL P-113-SK [1.53E+05 (CFU/mL)] or Sp-H5 [2.0E+04 (CFU/mL)], compared with BHI [2.62E+07 (CFU/mL)] (P<0.001, FIG. 4). However, only 87% *S. mutans* were killed by P-113 at 160 μmol/mL concentration.

Figure 5:
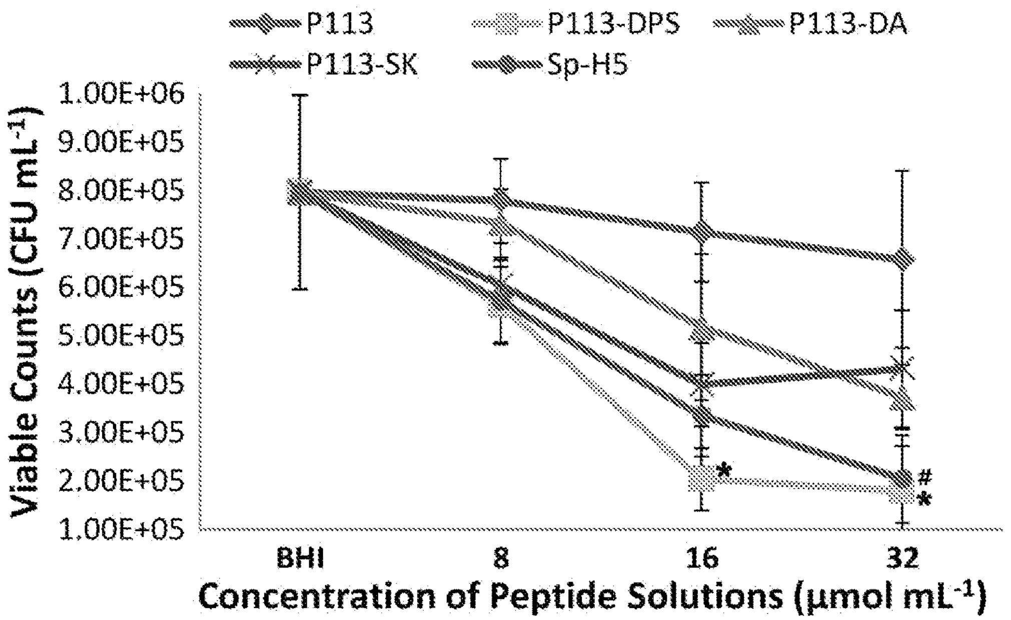
FIG. 5 is a graph showing viable counts of *S. mutans* on enamel surfaces coated with P-113, P-113-DPS, P-113-DA, P-113-SK, and Sp-H5 after 5 hours of incubation. *P<0.001, compared with BHI.

The CLSM images of the non-coated enamel surfaces revealed more live *S. mutans* in the control group than P-113-DPS-coated and Sp-H5-coated enamel surfaces (data not shown). Viable counts of *S. mutans* were significantly reduced with 16 μmol/mL P-113-DPS-coated [2.03E+05 (CFU/mL)] or 32 μmol/mL of Sp-H5-coated [2.04E+05 (CFU/mL)] enamel surfaces compared with non-coated enamel surfaces [7.96E+05 (CFU/mL)] (P<0.001, FIG. 5). Significant difference was not detected using different concentrations of P-113-DPS. No significant decrease was detected in other groups. Among all peptide solutions, P-113-DPS showed the most potent inhibitory effects on *S. mutans* adhesion at the lowest concentration tested (16 μmol/mL).

Demineralization and Remineralization Properties

Figure 6:
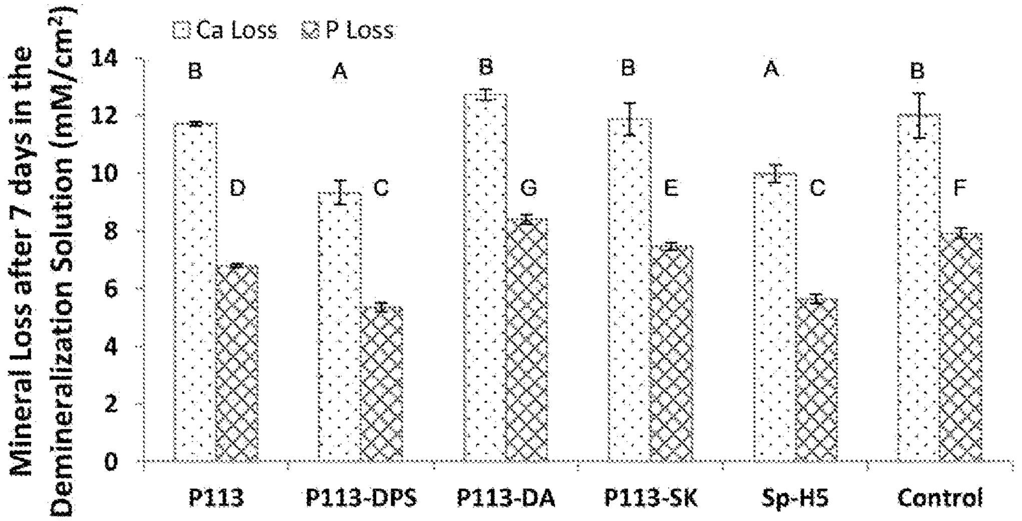
FIG. 6 is a graph showing the amount of Ca/P loss on enamel surfaces in the demineralization solutions after coating with the indicated peptides. The dotted bar indicates the Ca loss, and the crosshatched bar denotes the P loss. Different capital letters show significant differences (A<B, C<D<E<F<G, P<0.001).

After enamel surfaces were exposed to demineralization solutions for 7 days, the MicroCT graphs and 3D models of lesions in P-113, P-113-DPS, P-113-DA, P-113-SK, Sp-H5, and control group showed irregular morphology with various lesion areas and depths (data not shown). The maximum lesion depth in P-113, P-113-DPS, P-113-DA, P-113-SK, Sp-H5, and control group was 115 μm, 75 μm, 110 μm, 100 μm, 85 μm, and 115 μm, respectively. The cross-section of the lesion showed higher mineral density in the outermost layer than the one below in all groups. ICP-OES mineral quantification showed Ca and P loss from P-113-DPS-coated or Sp-H5-coated enamel slices decreased significantly compared with those from P-113-coated, P-113-DA-coated, P-113-SK-coated or non-coated enamel slices (P<0.001, FIG. 6). Significant differences were not detected in Ca losses between the control group and P-113, P-113-DA, or P-113-SK groups. For the selected peptide solutions, P-113-DPS and Sp-H5 demonstrated a stronger ability to inhibit demineralization.

Figure 7A:
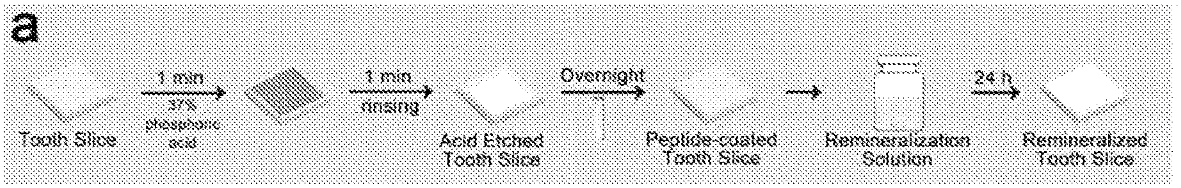
FIG. 7A is a schematic representation of the assay to determine mineral gain after 24 h in remineralization solutions.

After exposure of enamel surfaces to remineralization solutions for 24 h (FIG. 7A), the generation of new HA crystals as imaged by FE-SEM were formed on demineralized enamel slices in all groups. Cross-sectional micrographs of the remineralized enamel slices clearly showed a newly regenerated layer tightly conjoined to its underlying natural enamel. The thickness of the regenerated crystal layer on the enamel surface for P-113-DPS (8.5 μm) was qualitatively thicker than P-113 (6 μm), P-113-DA (7 μm), P-113-SK (7 μm), Sp-H5 (6 μm), and controls (4 μm). The crystal macrostructure of the regenerated layer formed needle-like projections and the crystal microstructure of the regenerated layer formed hexagonal prism-like projections, both of which are morphologically similar to natural enamel.

Figure 7B:
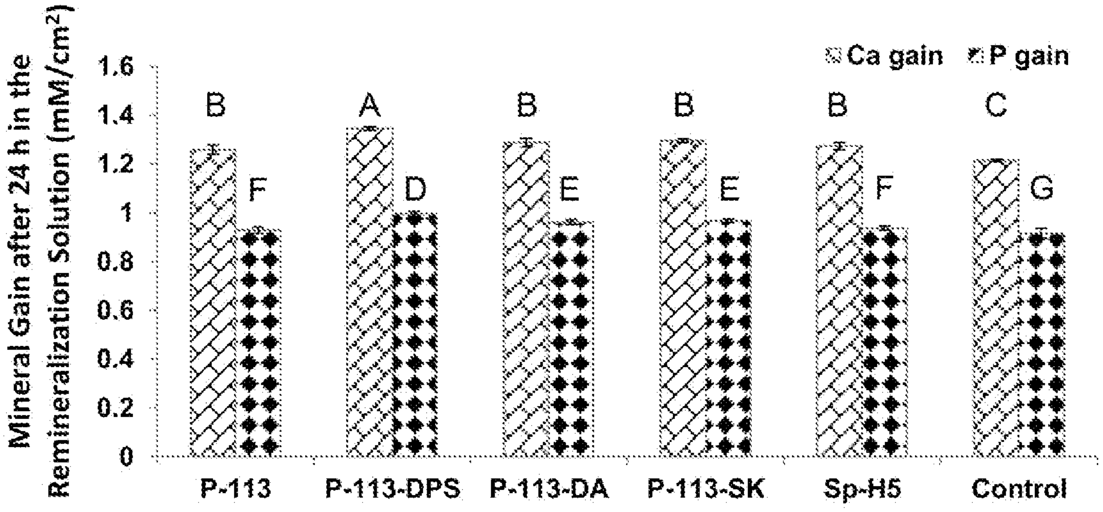
FIG. 7B is a graph showing the amount of Ca/P gain on enamel surfaces in the remineralization solutions after coating with the indicated peptides. The brick bar indicates the Ca gain, and the diamond bar denotes the P gain. Different capital letters show significant differences (A>B>C, D>F, D>G, E>G, P<0.001).

As shown in FIG. 7B, ICP-OES mineral quantification showed significant P gain in the P-113-DPS group compared with the control group (D>F, P<0.001), significant Ca gain in all treatment groups compared with the control group (B>C, P<0.001), and significant Ca gain in the P-113-DPS group compared with other groups (A>B, A>C, P<0.001).

Cytocompatibility

Figure 8A:
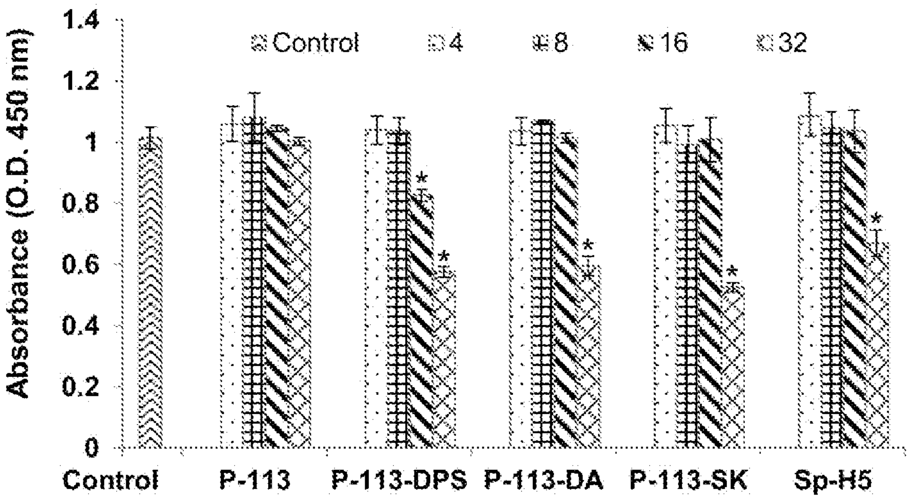
FIGS. 8A-8B show cytocompatibility evaluation of peptides using MC3T3-E1.
Figure 8B:
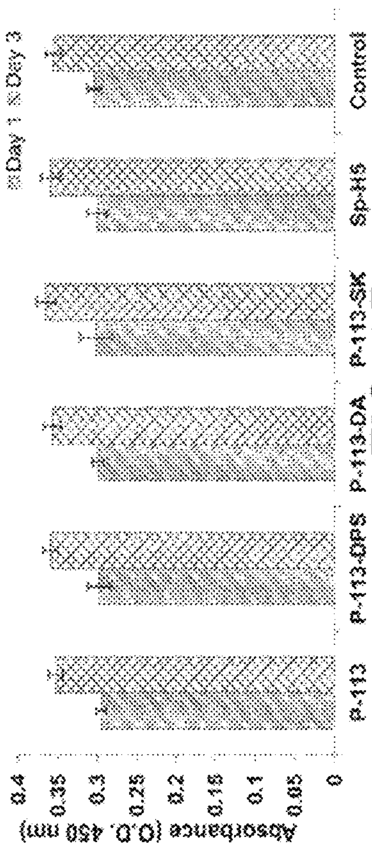

After 24 h of incubation, there was no significant absorbance difference in all concentrations of P-113; 4 and 8 μM mL$^{-1}$ P-113-DPS; 4, 8, and 16 μM mL$^{-1}$ P-113-DA; 4, 8, and 16 μM mL$^{-1}$ P-113-SK, compared with the control group (FIG. 8A). After 3 days incubation, MC3T3-E1 cell proliferation on 8 μM mL$^{-1}$ peptide-coated enamel surfaces was not significantly different among all groups (FIG. 8B). Results from fluorescent images were consistent with the quantitative CCK-8 assay. MC3T3-E1 cells were stained green and exhibited a spindle like morphology in all groups after 3 days incubation. During incubation for 3 days, 8 μM mL$^{-1}$ peptide-coated groups showed significantly increased numbers of live cell compared with the control group. These results indicated that at a concentration of 8 μM mL$^{-1}$, the peptides exhibited good cytocompatibility, and can be used for tooth surface applications.

MD Simulations—Adsorption of Peptides onto the HA System

Figure 9A:
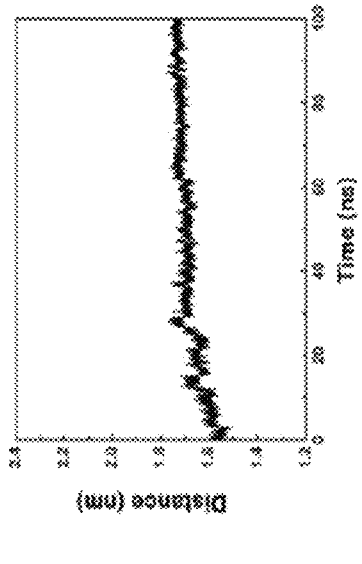
FIGS. 9A-9F are graphs showing the centroid distance between P-113 and HA (FIG. 9A), the binding energy between P-113 and HA (FIG. 9B), the binding energy between the Ca2+ (red), OH− (gray), and PO43− (blue) of HA and P-113 (FIG. 9C), P-113-DPS (FIG. 9D), P-113-DA (FIG. 9E), and P-113-SK (FIG. 9F), respectively.
Figure 9B:
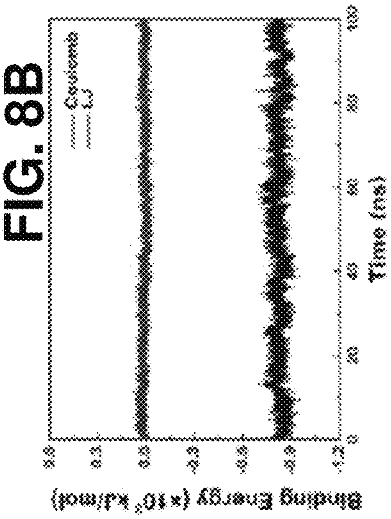
Figure 9C:
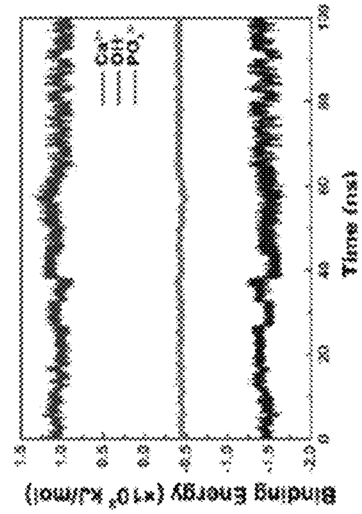
Figure 9D:
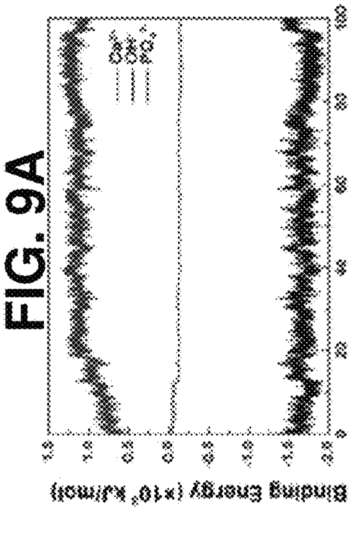
Figure 9E:
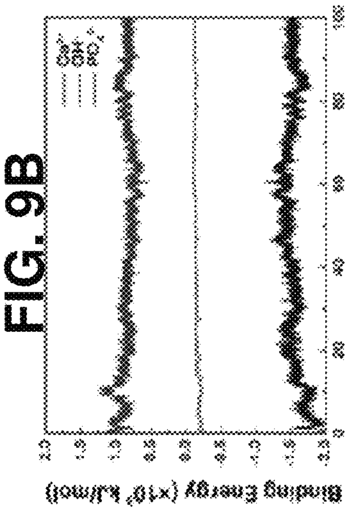
Figure 9F:
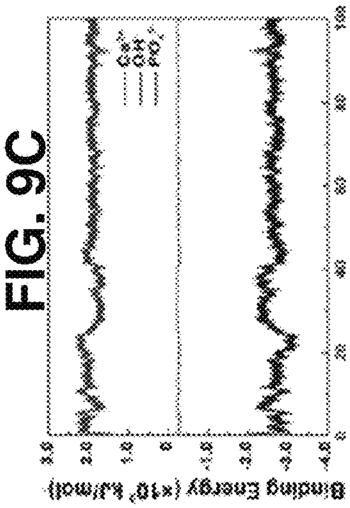
Figure 10A:
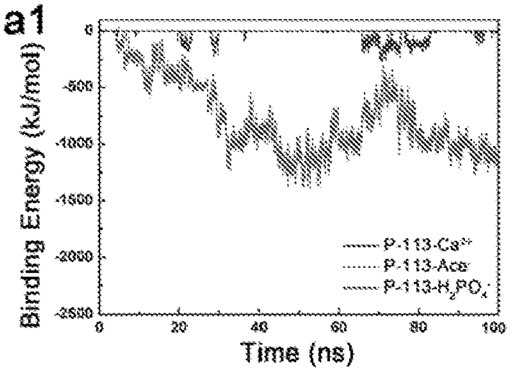
FIGS. 10A-10H are graphs showing the binding energy between P-113 and the ions (FIG. 10A), HA and the ions in the P-113-HA complex (FIG. 10B), P-113-DPS and the ions (FIG. 10C), HA and the ions in the P-113-DPS-HA complex (FIG. 10D), P-113-DA and the ions (FIG. 10E), HA and the ions in the P-113-DA-HA complex (FIG. 10F), P-113-SK and the ions (FIG. 10G), and HA and the ions in the P-113-SK-HA complex (FIG. 10H).
Figure 10B:
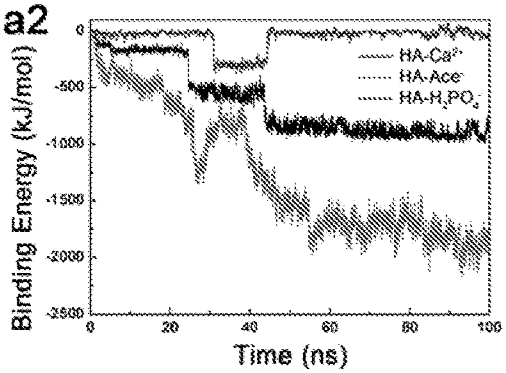
Figure 10C:
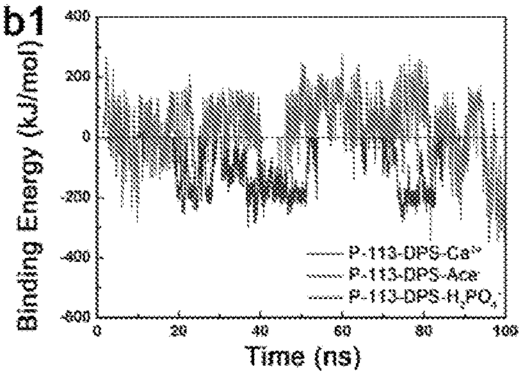
Figure 10D:
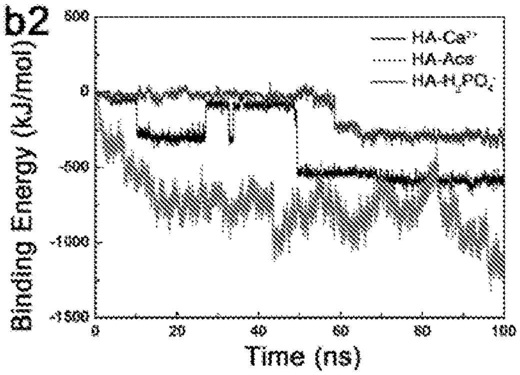
Figure 10E:
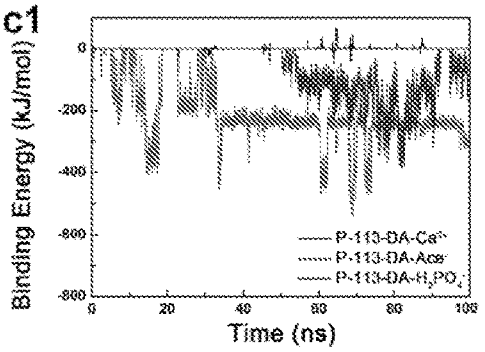
Figure 10F:
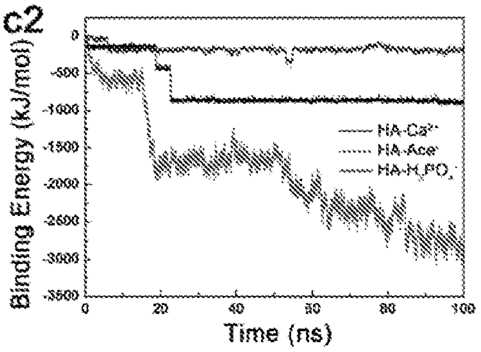
Figure 10G:
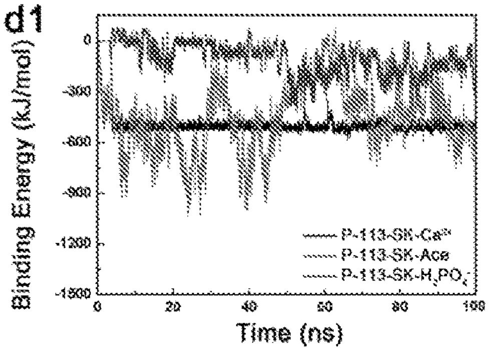
Figure 10H:
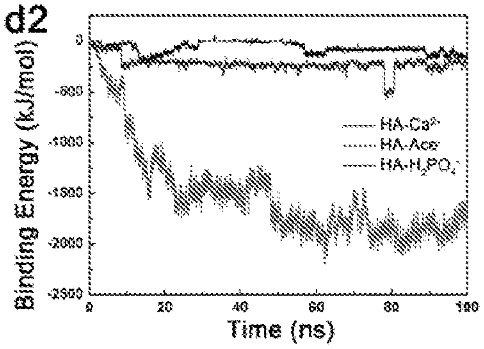
Figure 11A:
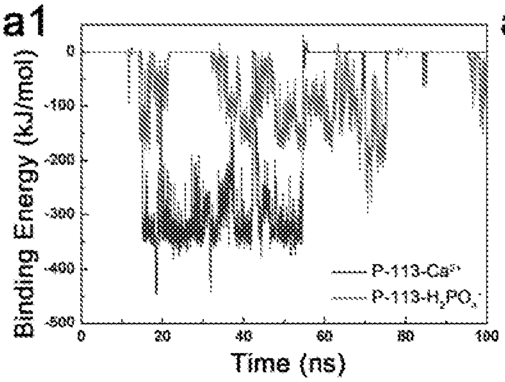
FIGS. 11A-11H are graphs showing the binding energy between P-113 and the ions (FIG. 11A), HA of the P-113-HA complex and the ions (FIG. 11B), P-113-DPS and the ions (FIG. 11C), HA of the P-113-DPS-HA complex and the ions (FIG. 11D), P-113-DA and the ions (FIG. 11E), HA of the P-113-DA-HA complex and the ions (FIG. 11F), P-113-SK and the ions (FIG. 11G), and HA of the P-113-SK-HA complex and the ions (FIG. 11H).
Figure 11B:
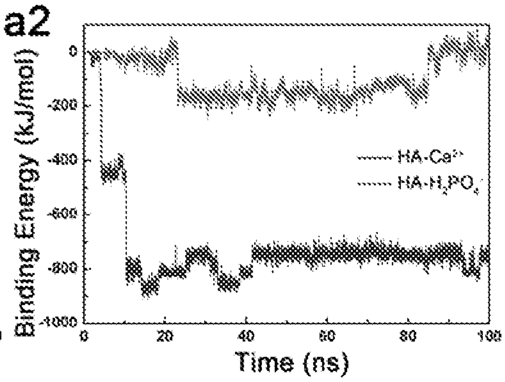
Figure 11C:
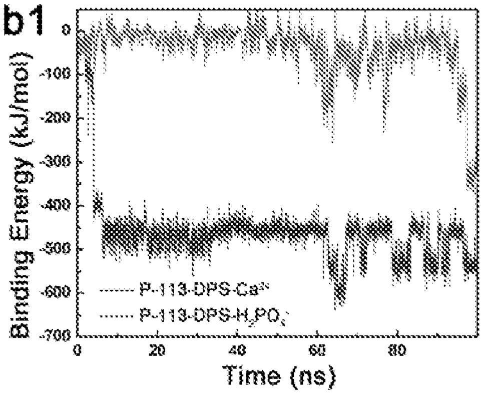
Figure 11D:
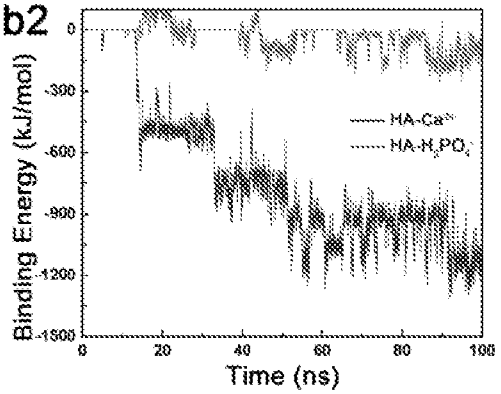
Figure 11E:
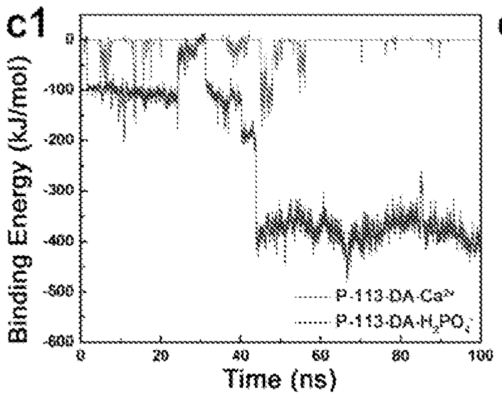
Figure 11F:
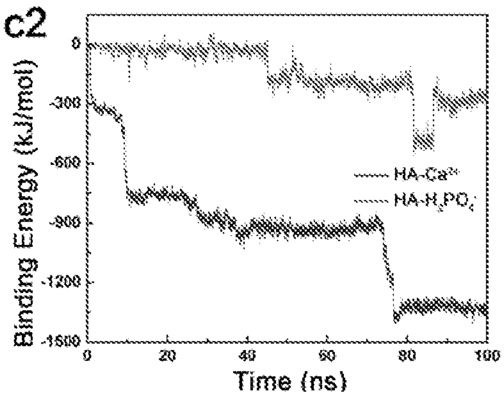
Figure 11G:
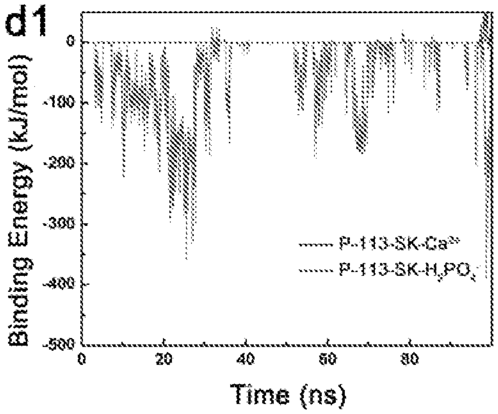
Figure 11H:
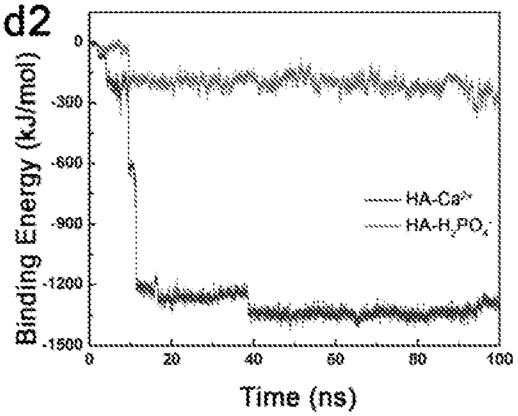

The centroid distance between P-113 and HA was within 1.6-2.4 nm without any large fluctuations evident (FIG. 9), indicating a high degree of binding stability between P-113 and HA. The Lennard-Jones potential was sustained horizontally (FIG. 9B, red curve), indicating no van der Walls forces in the P-113-HA adsorption system. However, the Coulombic potential decreased at the onset and quickly reached equilibrium (<5 ns) (FIG. 9B, blue curve), demonstrating the presence of electrostatic forces. The centroid distances and potential evaluations of the other peptide-HA adsorption systems were similar to the P-113-HA system. Electrostatic interaction was the main driving force in the adsorption system, and the adsorption process itself was fast (<5 ns). FIGS. 9C-9F show binding energies between the key constituents of HA and peptides (FIG. 9C, P-113; FIG. 9D, P-113-DPS; FIG. 9E, P-113-DA; and FIG. 9F, P-113-SK, respectively). The red curve initially rose, indicating the presence of repulsive forces between peptides and HA $Ca^{2+}$ ions. The blue curve decreased at the initial simulation time (<5 ns), indicating the presence of attractive forces between peptides and HA $PO_4^{3-}$ ions. There was a slight decrease in the gray curve, indicating few attractive forces between peptides and HA OH ions. After a comprehensive analysis of the various binding energies, negatively charged $PO_4^{3-}$ was the main functional component in HA contributing to the adsorption of peptides.

The stable and unique molecular conformations of peptide adsorption onto HA at 100 ns scale were examined. The positive charged amino acid residues Lys2, Arg3, Lys10, and amino-terminus in P-113 adsorbed to HA. The positive charged amino acid residues Lys2, Arg3, Arg9, Lys10, and amino-terminus in P-113-DPS adsorbed with HA, while there was a large distance between DPS and HA. A similar adsorption was found in P-113-DA (Lys2, His5, Arg9, Lys10, and amino-terminus) and HA when DA was separate from HA. Apart from Lys2, Arg3, Arg9, Lys10, and the amino-terminus, more positively charged amino acid residues Lys14, Lys16, Lys19, Lys21, Lys24, and Lys26 in P-113-SK adsorbed to HA. The electrostatic interaction between positive charged lysine, arginine, and the amino-terminus of the peptides and negative charged $PO_4^{3-}$ of the HA surface was the consistent binding pattern between peptides and HA. In comparing the binding energies of the four peptide-HA adsorption systems, the sequence of binding energies were as follows: P-113-SK (−1000 kJ/mol)<P-113-DA (−800 kJ/mol)=P-113 (−800 kJ/mol)<P-113-DPS (−700 kJ/mol).

The Peptide-HA Complexes in the Demineralization System

The average binding energies between ions ($Ace^-$, $Ca^{2+}$, and $H_2PO_4^-$) and the peptide-HA complexes in the demineralization system are illustrated in FIG. 10. The largest decrease in average binding energy observed was $Ace^-$ and HA, implicating $Ace^-$ as the most critical component to react with $Ca^{2+}$ of the HA in the demineralization system. The sequence of the average binding energy between $Ace^-$ and the peptide of the complexes was P-113-HA (−1000 kJ/mol) <P-113-SK-HA (−450 kJ/mol)<P-113-DA-HA (−200 kJ/mol)<P-113-DPS-HA (0 kJ/mol). The sequence of the average binding energy between $Ace^-$ and the HA of the complexes was P-113-DA-HA (−2800 kJ/mol)<P-113-HA (−1800 kJ/mol)=P-113-SK-HA (−1800 kJ/mol)<P-113-DPS-HA (−1200 kJ/mol).

The Peptide-HA Complexes in the Remineralization System

As shown in FIG. 11, the binding energy of $Ca^{2+}/H_2PO_4^-$ and HA of the peptide-HA complex fluctuates in a step-wise manner. A considerable decrease was observed in the binding energy between $Ca^{2+}/H_2PO_4^-$ and HA in the remineralization system. The sequence of the average binding energy between $Ca^{2+}$ and the HA of the complexes was P-113-DA-HA (−1400 kJ/mol)<P-113-SK-HA (−1350 kJ/mol)<P-113-DPS-HA (−1050 kJ/mol)<P-113-HA (−750 kJ/mol). The sequence of the average binding energy between $H_2PO_4^-$ and the HA of the complexes was P-113-DA-HA (−300 kJ/mol)<P-113-SK-HA (−200 kJ/mol)<P-113-HA (−150 kJ/mol)<P-113-DPS-HA (−100 kJ/mol). The sequence of the average binding energy between $Ca^{2+}$ and the peptide of the complexes was P-113-DPS-HA (−450 kJ/mol)<P-113-DA-HA (−350 kJ/mol)<P-113-HA (0 kJ/mol)=P-113-SK-HA (0 kJ/mol). There was no binding energy between $H_2PO_4^-$ and the peptides in the complexes.

Figure 12:
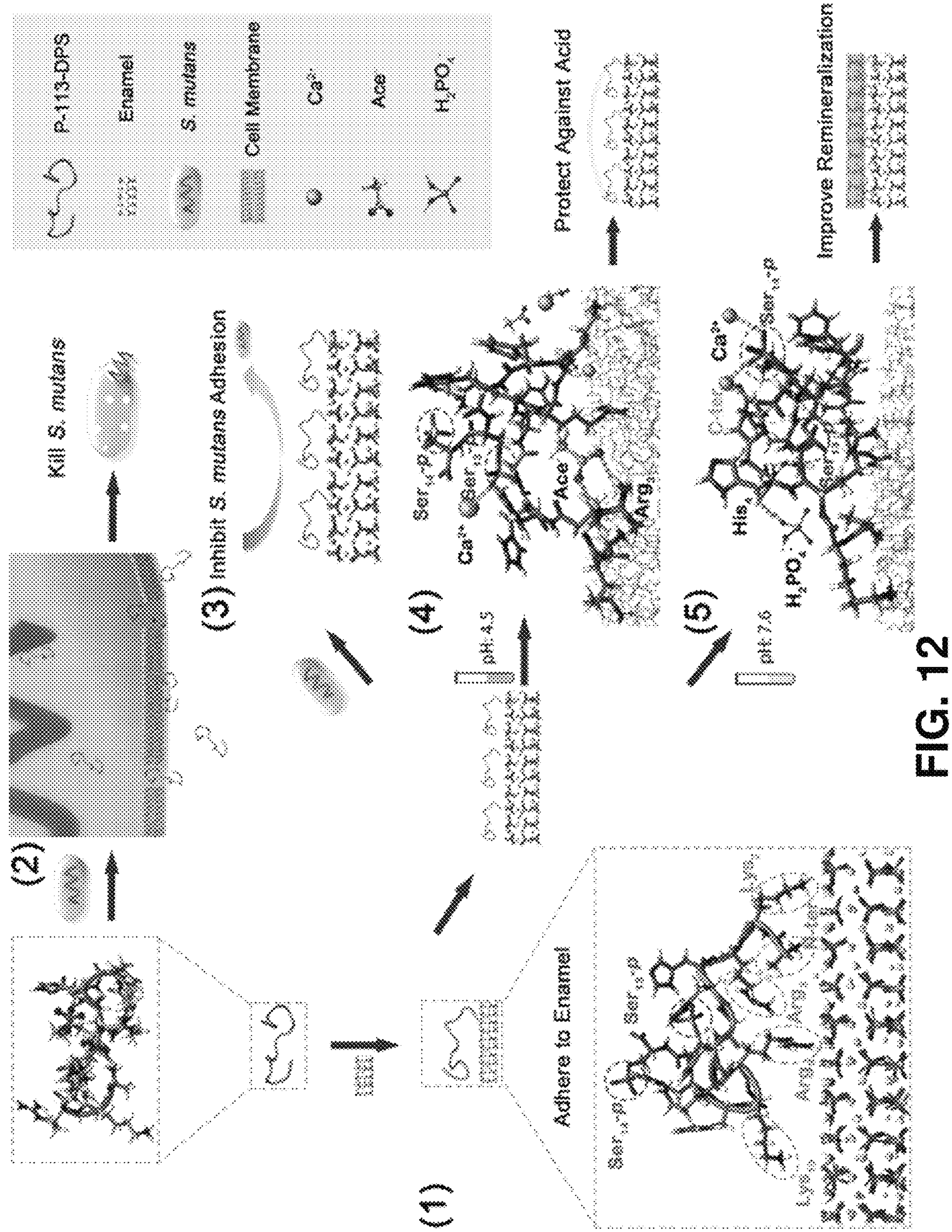
FIG. 12 is a schematic depicting mechanisms of action of P-113-DPS. (1) P-113-DPS adheres to the enamel surface via positively charged amino acids (blue circles: N-ter, Lys2, Arg3, Arg9, and Lys10) attracted to negatively charged PO43− of HA. (2) P-113-DPS kills planktonic *S. mutans*. (3) Coating of P-113-DPS on enamel inhibits the adhesion of *S. mutans*. (4) Coating of P-113-DPS on enamel protects the enamel surface against demineralization. (5) Coating of P-113-DPS on enamel increases the thickness of the regenerated crystal layer. Ser13-p and Ser14-p are in the red circles. Carboxyl is in the green circle. The green dotted lines represent coordinate bonds, and the pink dotted lines represent hydrogen bonds.

In summary, a dual-bioactive peptide, P-113-DPS, was constructed with anti-biofouling and mineralizing abilities. FIG. 12 is schematic diagram illustrating a hypothesized mechanism on how P-113-DPS confers its bioactivity. In Step 1, DPS with highlighted amino acid residues $Ser_{13}$-p and $Ser_{14}$-p is shown in the outermost layer of the P-113-DPS-HA adsorption system. P-113-DPS adheres to the enamel surface through electrostatic attraction forces between positively charged amino acid residues $Lys_2$, $Arg_3$, $Arg_9$, $Lys_{10}$, and amino-terminus in P-113-DPS and negatively charged $PO_4^{3-}$ of enamel. In Step 2, P-113-DPS is destructive against planktonic *S. mutans* and *S. mutans* biofilm by localizing at the bacterial surface, cross-linking with bacterial membrane phospholipids, and increasing the permeability of the membrane and forming perforations. In Step 3, the coating of P-113-DPS on enamel inhibits the adhesion of *S. mutans* through preferential occupation for binding sites in addition to its inherent antibacterial ability. In Step 4, $Arg_3$ is attracted to $Ace^-$ while $Ser_{13}$-p attracts to $Ca^{2+}$ in compensation. $Ser_{14}$-p with negative charges is in the outermost layer. Coating of P-113-DPS on enamel protects the enamel surface against the acid microenvironment via the electrostatic repulsive force of DPS in the outermost layer and space occupancy of P-113-DPS on the enamel surface. In Step 5, $Ser_{14}$-p and carboxyl are attracted to $Ca^{2+}$ by coordinate bonding and $His_4$ to $H_2PO_4^-$ by hydrogen bonding. Although $Ser_{13}$-p does not attract to $Ca^{2+}$ in this image, it does have the opportunity to attract $Ca^{2+}$ during these reactions, which might occur in another time.

Coating of P-113-DPS on the demineralized enamel surface attracts more $Ca^{2+}$ from the remineralization solution and quickly induces nucleation and hexagonal prism-like crystal growth due to the presence of DPS.

It is understood that the disclosed methods and compositions are not limited to the particular methodology, protocols, and reagents described as these can vary. It is also to be understood that the terminology used herein is for the purpose of describing particular embodiments only, and is not intended to limit the scope of the present invention which will be limited only by the appended claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a step is disclosed and discussed and a number of modifications that can be made to a number of components including the step are discussed, each and every combination and permutation of step and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in algorithms or methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a," "an," and "the" include plural reference unless the context clearly dictates otherwise.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. can include numerous options and alternatives, this should not be construed as, and is not an admission that, such options and alternatives are equivalent to each other or, in particular, are obvious alternatives.

Every composition disclosed herein is intended to be and should be considered to be specifically disclosed herein. Further, every subgroup that can be identified within this disclosure is intended to be and should be considered to be specifically disclosed herein. As a result, it is specifically contemplated that any composition, or subgroup of compositions can be either specifically included for or excluded from use or included in or excluded from a list of compositions.

Those skilled in the art will recognize, or be able to ascertain using no more than routine experimentation, many equivalents to the specific embodiments of the method and compositions described herein. Such equivalents are intended to be encompassed by the following claims.

We claim:

1. An isolated peptide comprising an antimicrobial domain and a phosphoserine domain, wherein the antimicrobial domain comprises a histatin 5 segment, wherein the histatin 5 segment comprises a histatin 5 protein, a variant thereof, a portion thereof, or a variant of a portion thereof, wherein the phosphoserine domain comprises a phosphorylated serine, wherein upon contact with a tooth, the isolated peptide binds to the tooth enamel, reduces or prevents tooth decay, reduces or prevents bacterial biofilm formation on the tooth surface, reduces or prevents dental plaque formation, reduces or prevents bacterial adhesion to the tooth surface, induces or increases mineralization, or combinations thereof, and (a) wherein the phosphoserine domain comprises two or more phosphorylated serines, or (b) wherein the phosphoserine domain is at the C-terminus of the isolated peptide.

2. The peptide of claim 1, wherein the antimicrobial domain comprises AKRHHGYKRKFH (SEQ ID NO:2) or a sequence comprising at least 90% sequence identity to AKRHHGYKRKFH (SEQ ID NO:2).

3. The peptide of claim 1, wherein the histatin 5 segment comprises the sequence DSHAKRHHGYKRKFHEKHHSHRGY (SEQ ID NO:1) or a sequence comprising at least 90% sequence identity to DSHAKRHHGYKRKFHEKHHSHRGY (SEQ ID NO: 1).

4. The peptide of claim 1, wherein the phosphoserine domain comprises two or more phosphorylated serines.

5. The peptide of claim 1, wherein the phosphoserine domain is at the C-terminus of the isolated peptide.

6. The peptide of claim 4, wherein the peptide comprises the sequence AKRHHGYKRKFH-SpSp (SEQ ID NO:4), wherein each Sp independently represents a phosphorylated serine.

7. An oral care composition or device comprising the isolated peptide of claim 1.

8. The oral care composition or device of claim 7 comprising a plurality of copies of the isolated peptide.

9. The oral care composition or device of claim 8 further comprising a pharmaceutically acceptable excipient, wherein the excipient is suitable for administration to oral cavity.

10. The oral care composition or device of claim 8, wherein the composition or device is selected from mouthwash, toothpaste, dental cream, oral spray, a rinse, a gargle, a gum, a tablet, an oral lozenge, dental floss, a tooth whitening strip or solution, a cleaning solution, a toothpick, a toothbrush, a varnish, or composite resin.

11. A method comprising applying the oral care composition or device of claim 8 to teeth and/or oral cavity of a subject.

12. A method of reducing, preventing, and/or repairing tooth decay in a subject in need thereof, the method comprising contacting the subject's teeth and/or oral cavity with a peptide comprising the sequence AKRHHGYKRKFH-SpSp (SEQ ID NO:4) or a sequence comprising at least 90% sequence identity to AKRHHGYKRKFH-SpSp (SEQ ID NO:4).

13. A method of reducing or preventing enamel demineralization and/or promoting enamel mineralization in a subject in need thereof, the method comprising contacting the subject's teeth and/or oral cavity with a peptide comprising the sequence AKRHHGYKRKFH-SpSp (SEQ ID NO:4) or a sequence comprising at least 90% sequence identity to AKRHHGYKRKFH-SpSp (SEQ ID NO:4).

14. The method of claim 12, wherein the peptide is comprised in composition or device selected from mouthwash, toothpaste, dental cream, oral spray, a rinse, a gargle, a gum, a tablet, an oral lozenge, dental floss, a tooth whitening strip or solution, a cleaning solution, a toothpick, a toothbrush, a varnish, or composite resin, wherein the composition or device comprises a plurality of copies of the peptide.

15. The method of claim 12, wherein the peptide is in an amount effective to reduce or prevent tooth decay, reduce or prevent bacterial biofilm formation, reduce or prevent dental plaque formation, reduce or prevent bacterial adhesion to tooth surfaces, inhibit growth and/or proliferation of oral bacteria, induce or increase enamel mineralization, or combinations thereof.

16. The method of claim 15, wherein the bacteria is selected from *Streptococcus mutans, Streptococcus faecalis, Streptococcus sobrinus, Lactobaccilus acidophilus, Lactobacillus casei*, or combinations thereof.

* * * * *